United States Patent
Pearson et al.

(10) Patent No.: US 7,160,296 B2
(45) Date of Patent: *Jan. 9, 2007

(54) TISSUE ABLATION APPARATUS AND METHOD

(75) Inventors: Rob Pearson, San Jose, CA (US); Steve A. Daniel, Fremont, CA (US); Daniel J. Balbierz, Redwood City, CA (US); Kee S. Lee, Newark, CA (US); Jessica Liang, Redwood City, CA (US); Martha Getaneh, San Jose, CA (US)

(73) Assignee: Rita Medical Systems, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/142,713

(22) Filed: May 10, 2002

(65) Prior Publication Data
US 2003/0212394 A1 Nov. 13, 2003

Related U.S. Application Data

(60) Provisional application No. 60/290,060, filed on May 10, 2001.

(51) Int. Cl.
*A61B 18/18* (2006.01)
(52) U.S. Cl. .......................... 606/42; 607/102
(58) Field of Classification Search ................ 606/41, 606/42, 45–50; 607/101–105, 113, 116
See application file for complete search history.

(56) References Cited

U.S. PATENT DOCUMENTS

| | | | |
|---|---|---|---|
| 5,007,908 A | | 4/1991 | Rydell |
| 5,334,193 A | | 8/1994 | Nardella |
| 5,370,675 A | | 12/1994 | Edwards et al. |
| 5,472,441 A | * | 12/1995 | Edwards et al. ............ 606/41 |
| 5,536,267 A | * | 7/1996 | Edwards et al. ............ 606/41 |
| 5,683,384 A | | 11/1997 | Gough et al. |
| 5,782,827 A | | 7/1998 | Gough et al. |
| 5,855,576 A | * | 1/1999 | LeVeen et al. .............. 606/41 |
| 5,868,740 A | | 2/1999 | LeVeen et al. |
| 5,980,517 A | * | 11/1999 | Gough ........................ 606/41 |
| 6,454,765 B1 | | 9/2002 | LeVeen et al. |

(Continued)

FOREIGN PATENT DOCUMENTS

DE        2124684        11/1972

(Continued)

*Primary Examiner*—Michael Peffley
(74) *Attorney, Agent, or Firm*—Jacqueline F. Mahoney; Peter J. Dehlinger; Perkins Coie LLP

(57) ABSTRACT

A tissue-ablation method and apparatus are disclosed. The apparatus includes a plurality of RF ablation electrodes, and a plurality of sensor elements, each movable from retracted to deployed positions in a tissue to be ablated. A control device in the apparatus is operatively connected to the electrodes for supplying an RF power to the electrodes, to produce tissue ablation that advances from individual-electrode ablation regions to fill a combined-electrode ablation volume. The control device is operatively connected to the sensor elements for determining the extent of ablation in the regions of the sensor elements. The supply of RF power to the electrodes can thus be regulated to control the level and extent of tissue ablation throughout the combined-electrode volume. The electrodes are preferably hollow-needle electrodes through which liquid can be infused into the tissue, also under the control of the control unit, to modulate and optimize tissue ablation.

28 Claims, 30 Drawing Sheets

U.S. PATENT DOCUMENTS

| | | |
|---|---|---|
| 6,468,273 B1 | 10/2002 | LeVeen et al. |
| 6,551,311 B1 * | 4/2003 | Lee et al. .................... 606/41 |
| 6,575,967 B1 | 6/2003 | LeVeen et al. |
| 6,622,731 B1 * | 9/2003 | Daniel et al. ............... 128/898 |
| 2002/0026127 A1 | 2/2002 | Balbierz et al. |
| 2002/0026188 A1 | 2/2002 | Balbierz et al. |
| 2002/0077627 A1 | 6/2002 | Johnson et al. |
| 2003/0109871 A1 * | 6/2003 | Johnson et al. ............... 606/42 |

FOREIGN PATENT DOCUMENTS

| | | |
|---|---|---|
| NL | 1003793 | 8/1996 |
| WO | WO 01/74251 | * 10/2001 |
| WO | WO 01/74251 A2 | 10/2001 |

* cited by examiner

TISSUE ABLATION APPARATUS AND METHOD

This application claims the benefit of U.S. Provisional Application No. 60/290,060 filed May 10, 2001, which is incorporated herewith by reference in its entirety.

FIELD OF THE INVENTION

This invention relates generally to a method for treating tissue, tissue masses, tissue tumors and lesions. More particularly, the invention relates to an apparatus and method for minimally invasive therapeutic treatment of tumors and tissue mass. Still more particularly, the invention relates to a method and apparatus utilizing fluid to enhance the delivery of energy to tumor and tissue masses to produce larger, faster ablation volumes with improved clinical outcomes.

BACKGROUND OF THE INVENTION

Current methods for treating tumors using RF energy have several key shortcomings including incomplete ablation volumes, small ablation volumes, tissue desiccation and charring or protracted ablation times. The present invention provides a method and apparatus to solve these and other related problems.

SUMMARY OF THE INVENTION

The invention includes, in one aspect, a tissue-ablation apparatus composed of an elongate delivery device having a lumen terminating at a distal end and a plurality of electrodes carried in the device for movement between retracted positions at which the electrodes are disposed within the device's lumen, and deployed positions at which the electrodes are deployed from the distal end at a plurality of arcuate, laterally extending, angularly spaced positions. Each deployed electrode defines an individual-electrode ablation volume which, in the early phases of ablation, is proximate to that electrode when an RF current is applied to that electrode, with such deployed in tissue, where contained application of RF current to the electrodes causes the individual-electrode ablation volumes to grow and merge with each other to form a combined-electrode ablation volume.

Also in the apparatus is a plurality of elongate sensor elements carried in the device for movement between retracted positions at which the sensor elements are disposed within the device's lumen, and deployed positions at which the sensor are deployed from the distal end at a plurality of angularly spaced positions within the volume corresponding to the combined-electrode ablation volume.

A control device or unit in the apparatus is operatively connected to the electrodes and to the sensor elements for (i) supplying an RF power to the electrodes, with such deployed in tissue, to produce tissue ablation that advances from the individual-electrode ablation volumes to fill the combined-electrode ablation volume, and (ii) determining the extent of ablation in the regions of the sensor elements. The supply of RF power to the electrodes can thus be regulated to control the level and extent of tissue ablation throughout the combined-electrode volume.

The electrodes and sensor elements may be operatively connected for movement as a unit from their retracted to their deployed positions. Alternatively, the electrodes may be movable from their retracted to their retracted and deployed positions independent of the movement of the sensor elements from their retracted and deployed positions.

The sensor elements are in their deployed positions may be disposed outside of the individual-electrode ablation volumes, preferably midway between pairs of adjacent electrodes in their deployed state.

In one embodiment, the sensor elements are conductive wires, and the control device is operable to determine the impedance of tissue in the regions of the wires, as a measure of extent of ablation in the region of the sensor elements.

In another embodiment, the sensor elements have thermal sensors, and the control device is operable to determine tissue temperature in the region of the thermal sensors, as a measure of the extent of ablation in the region of the sensor elements.

In still another embodiment, the sensor elements are optical fibers, and the control device is operable to determine optical properties in the region of the fibers, as a measure of the extent of ablation in the region of the sensor elements.

The electrodes may be hollow-needle electrodes, allowing liquid to be injected through said electrodes into tissue, with the electrodes deployed in tissue. An exemplary liquid is an electrolyte, such as a physiological salt solution. In a preferred embodiment, the electrodes are designed to allow controlled fluid flow through each electrode individually.

Each infusion electrode may have a plurality of infusion ports along its distal end regions, and may be covered by a sheath that is axially movable between deployment and infusion positions at which the infusion ports are covered and exposed, respectively.

The control unit may include a display function for displaying to a user the extent of ablation of in the regions of the sensor elements, and an adjustable function, such as an RF power function, or liquid-infusion function, by which the user can adjust or modulate the rate or extent of ablation by modulating power level or amount of liquid infused into the ablation volume. Preferably the power of infusion functions can be controlled at the level of the individual electrodes, allowing for control over the rate and extent of individual-electrode volumes during the ablation procedure.

Alternatively, or in addition, the control unit may automatically control the power level and/or rate of infusion of liquid to one or more electrodes, during an ablation procedure, to modulate the rate and/or extent of individual regions of the desired ablation volume, for example, to ensure a uniform rate and extent of ablation throughout the desired combined-electrode ablation volume. In one general embodiment, the electrodes, when deployed, are positioned near the center of the faces of a platonic solid that defines a desired combined-electrode ablation volume. The number of faces of the platonic solid, and therefore the number of electrodes deployed will be determined, for example, by the size of the desired ablation volume. The sensor elements, when deployed, may be positioned near the vertices of the platonic solid. For example, for ablating a substantially spherical volume that circumscribes a pyramid, the apparatus may have four electrodes that are positioned near the center of the faces of the pyramid when deployed, and four sensors that are placed near the vertices of the pyramid when deployed.

In another aspect, the invention includes a method for ablating a selected volume of tissue in a patient. The method includes inserting into the tissue, a tissue-ablation apparatus having (a) an elongate delivery device with a lumen terminating at a distal end, and (b) a plurality of hollow-needle electrodes carried in the device for movement between retracted positions at which the electrodes are disposed within the device's lumen, and deployed positions at which the electrodes are deployed from the distal end at a plurality of arcuate, laterally extending, angularly spaced positions. The electrodes, in their deployed positions, define the selected tissue volume to be ablated. Liquid, such as an electrolyte is introduced into the tissue through the hollow-needle electrodes, by separately controlling the rate of liquid flow through each hollow-needle electrode. RF power is applied to the electrodes, to produce RF ablation of the tissue.

The liquid may be introduced at substantially equal flow rates through each electrode. An electrolyte having a desired electrolyte concentration may be selected. The liquid may be introduced prior to, during, or following the RF ablation step.

The method may further include monitoring the extent of ablation in the tissue volume during said applying step, and adjusting the rate at which liquid is introduced through individual hollow-needle electrodes in response to the monitoring, for example, to produce a uniform rate and extent of ablation throughout tissue volume being ablated.

These and other objects and features of the invention will become more fully apparent when the following detailed description of the invention is read in conjunction with the accompanying drawings.

BRIEF DESCRIPTION OF THE DRAWINGS

FIGS. 9a–9h are lateral views illustrating various configurations of the electrode including ring-like, ball, hemispherical, cylindrical, conical and needle-like.

FIG. 28a illustrates a standard trocar having a sharpened leading edge; FIG. 28b illustrates an embodiment of a trocar configured with a leading inner edge; and FIG. 28c illustrates an embodiment of a trocar having a coated leading inner edge.

DETAILED DESCRIPTION

Embodiments of the present invention provide the benefit of a method and apparatus to treat tumors and lesions such as hepatic tumors by utilizing conductivity enhancing solutions to deliver ablative electromagnetic energy to produce faster, larger and more consistent ablation volumes than by conventional means However one of the potential problems in infusing fluids through a hollow tube or hollow electrode is plugging of the electrode fluid lumen as the electrode is inserted into tissue, or a resulting of tissue coagulation from heating of the electrode during energy delivery or a combination of both. Further embodiments of the present invention provide a number of solutions to problem of tissue plugging of electrodes and infusion lumens occurring during insertion of the electrode into tissue or during the delivery of ablative energy.

Figure 1:
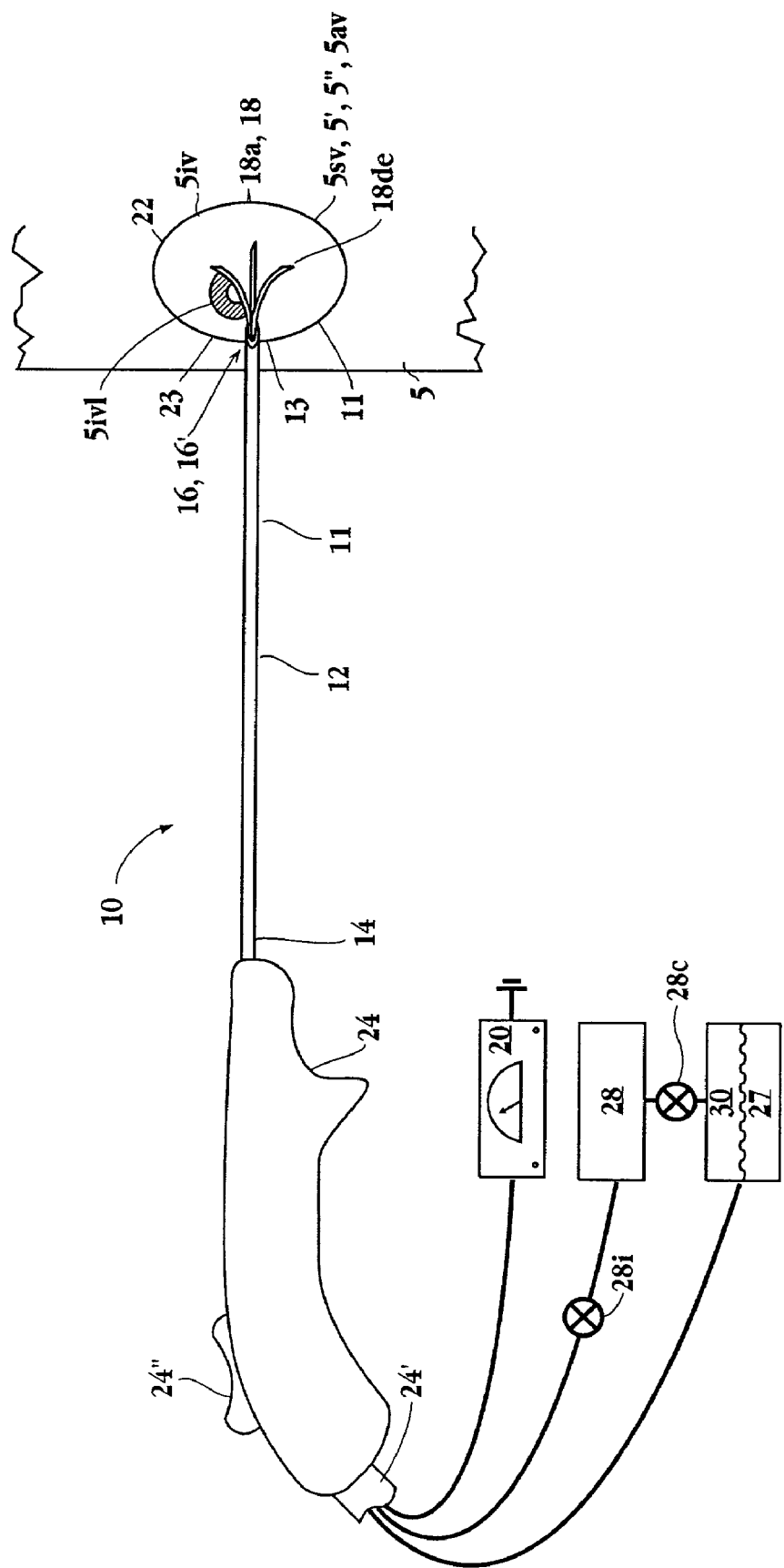
FIG. 1 is a perspective view illustrating the placement and deployment of an embodiment of a tissue infusion ablation apparatus for the treatment of tumors.

An embodiment of a tissue infusion ablation apparatus 10 to treat tumors and lesions is shown in FIG. 1. The apparatus is configured to be positioned at a bone tissue site 5' to treat or ablate a tumor or lesion 5". Tissue site 5' can be located in any location in various tissue including but not limited to liver, bone, breast, brain and lung. The apparatus can be configured to treat a number of lesions and ostepathologies including but not limited to metastatic lesions, osteolytic lesions, osteoblastic lesions, tumors, fractures, infected site, inflamed sites and the like. Once positioned at target tissue site 5', apparatus 10 can be configured to treat and ablate tissue at that site as well as collect a tissue sample using a bone biopsy device described herein or known in the art.

Figure 2:
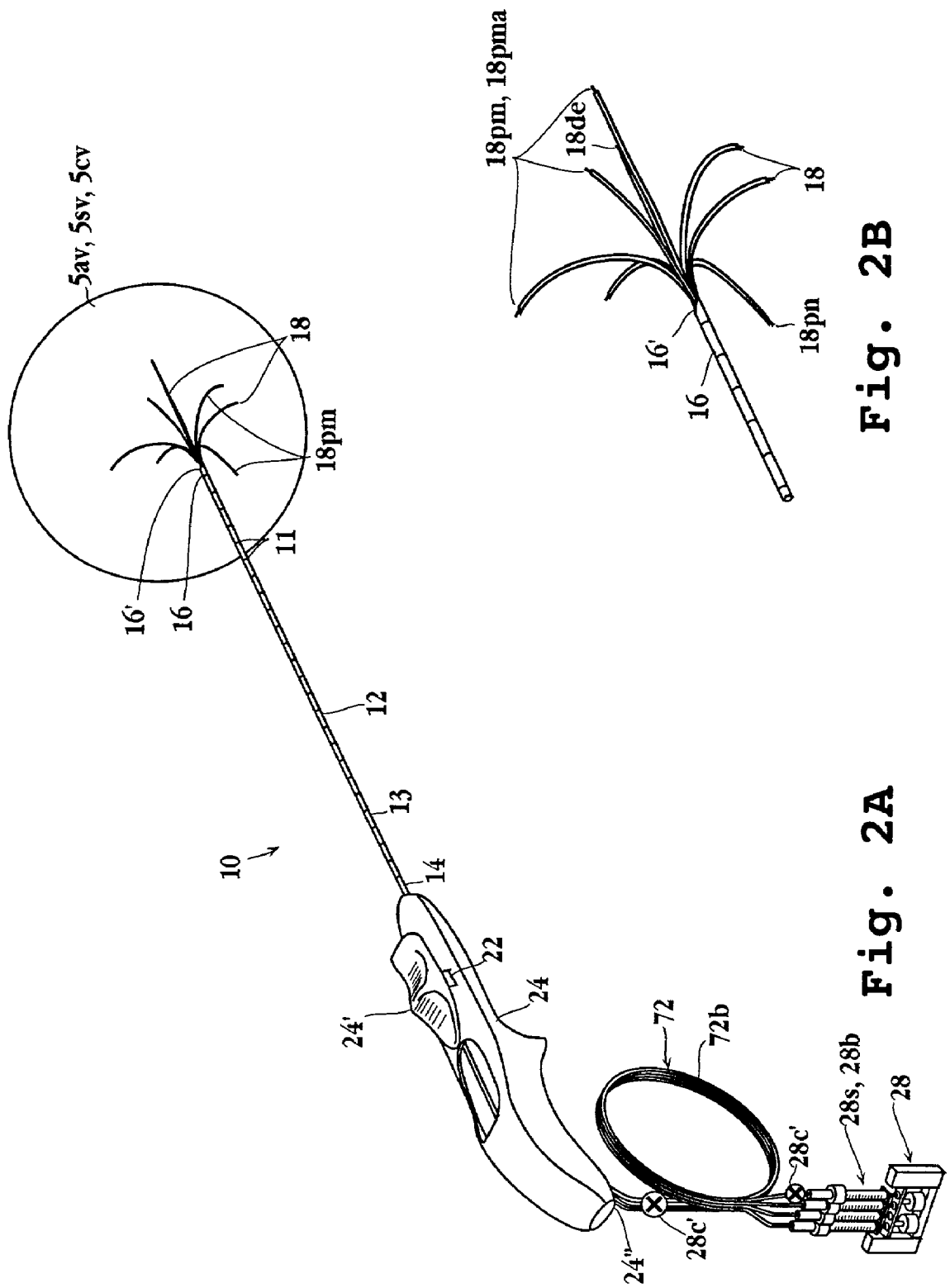
FIGS. 2a and 2b are perspective views illustrating the key components of a tissue infusion ablation including configurations of the infusion device having multiple syringes and multi-channel tubing.

Referring now to FIG. 2, an embodiment of a tissue infusion ablation apparatus 10 includes an elongated member or shaft 12 with a proximal end 14, a distal end 16, and an internal lumen extending therebetween or at least through a portion of the distal end region. Distal end 16 may be sufficiently sharp to penetrate tissue including bone, cartilage, muscle and fibrous and/or encapsulated tumor masses. In an embodiment, distal end 16 can be a needle that is integral or otherwise coupled to introducer 12 by joining means known in the art such as adhesive bonding, soldering, RF welding, crimping and the like. Shaft 12 may have one or more lumens 13 that may extend over all or a portion of its length. An energy delivery device, generally denoted as 18, is coupled to distal end 16'. Energy delivery device 18 can be configured to be coupled to an energy or power source 20. A sensor 22 may be coupled to shaft 12 including distal end 16' and energy delivery device 18.

For ease of discussion, shaft 12 will now be referred to as an introducer or delivery device 12, but all other embodiments discussed herein are equally applicable. Referring now to FIGS. 1–4, in various embodiments, introducer 12 can also be coupled at its proximal end 14 to a handle or handpiece 24. The shaft or introducer is also referred to herein as an elongate delivery device. All or portions of handpiece 24 can be detachable and can include ports 24' and actuators 24". Ports 24' can be coupled to one or more lumens 13 and can include fluid and gas ports/connectors and electrical, optical connectors. In various embodiments, ports 24' can be configured for aspiration (including the aspiration of tissue), and the delivery of cooling, conductivity enhancing, electrolytic, irrigation, polymer and other fluids (both liquid and gas) described herein. Ports 24' can include but are not limited to luer fittings, valves (one-way, two-way), toughy-bourst connectors, swage fittings and other adaptors and medical fittings known in the art. Ports 24' can also include lemo-connectors, computer connectors (serial, parallel, DIN, etc) micro connectors and other electrical varieties well known to those skilled in the art.

Further, ports 24' can include opto-electronic connections which allow optical and electronic coupling of optical fibers and/or viewing scopes (such as an orthoscope) to illuminating sources, eye pieces, video monitors and the like. Actuators 24" can include rocker switches, pivot bars, buttons, knobs, ratchets, cams, rack and pinion mechanisms, levers, slides and other mechanical actuators known in the art, all or portion of which can be indexed. These actuators can be configured to be mechanically, electro-mechanically, or optically coupled to pull wires, deflection mechanisms and the like allowing selective control and steering of introducer 12. Hand piece 24 can be coupled to tissue aspiration/collection devices 26, fluid delivery devices 28 (e.g. infusion pumps) fluid reservoirs (cooling, electrolytic, irrigation etc) 30 or power source 20 through the use of ports 24'. Tissue aspiration/collection devices 26 can include syringes, vacuum sources coupled to a filter or collection chamber/bag. Fluid delivery device 28 can include medical infusion pumps, Harvard pumps, peristaltic pumps, syringe pumps, syringes and the like.

Referring back to FIG. 2, in various embodiments fluid delivery device can be a syringe pump configured with multiple syringes 28s, multiple-bore syringes 28b with each syringe coupled to a separate fluid lumen or channel 72 directly or via a valve such as an indexing valve 28i. Related embodiments of infusion device 28 can include an indexing valve 28i as well as multi-lumen tubing or multichannel tubing 72b (which can be made from PEBAX, silicone or other resilient polymer) connected to one or more lumens 72 via lumen 13 or other channel within external to introducer 12.

In various embodiments, at least portions of tissue infusion ablation apparatus 10 including introducer 12 and distal end 16 may be sufficiently radiopaque to be visible under fluoroscopy and the like and/or sufficiently echogenic to be visible using ultrasonography. In specific embodiments, introducer 12 can include radiopaque, magnopaque or echogenic markers 11, at selected locations including along all or portions of introducer 12 including distal end 16'. Markers 11 can be disposed along introducer 12 to facilitate identification and location of tissue penetrating portion 16 including tissue collection portions, ports, sensors as well as other components and sections of tissue infusion ablation apparatus 10 described herein. In an embodiment, markers 11 can be ultrasound emitters known in the art. Also tissue infusion ablation apparatus 10 can include imaging capability including, but not limited to, fiber optics, viewing scopes such as a orthoscope, an expanded eyepiece, video imaging devices, ultrasound imaging devices and the like.

In various embodiments, apparatus 10 can be configured to be percutaneously introduced into tissue through a trocar, biopsy device, or orthoscope or other percutaneous or surgical access device known in the art. For any of these devices, apparatus 10 can be introduced with the aid of a guide wire 15 which introducer 12 is configured to track over. Guide wire 15 can be any of a variety of flexible and/or steerable guide wires or hypotubes known in the art. Introducer 12 can have sufficient length to position distal tip 16' in any portion or lobe of the bone 5 using either a percutaneous or a bronchial/transoral approach. The length of introducer 12 can range from 5 to 180 cm with specific embodiments of 20, 40, 80, 100, 120 and 140 cm. A preferred range includes 25 to 60 cm. The length and other dimensional aspects of introducer 12 can also be configured for pediatric applications with a preferred range in these embodiments of 15 to 40 cm. The diameter of introducer 12 can range from 0.020 to 0.5 inches with specific embodiments of 0.05, 0.1 and 0.3 inches as well as 1, 3, 6, 8 and 10 french sizes as is known in the art. Again, the diameter can be configured for pediatric applications with pediatric sizes of 1, 3 and 6 french. In various embodiments, the diameter of distal end 16 can range from 0.010 to 0.1 inches, with specific embodiments of 0.020, 0.030 and 0.040 inches. The diameter of distal end 16' can be configured to be positioned in various anatomical ducts, vasculature and bronchioles, such embodiment includes diameters of 0.40" or smaller.

In various embodiments, introducer 12 can be a catheter, multi-lumen catheter, or a wire-reinforced or metal-braided polymer shaft, port device (such as those made by the Heartport® Corp., Redwood City, Calif.), subcutaneous port or other medical introducing device known to those skilled in the art. In a specific embodiment introducer 12 is a trocar or a safety trocar and the like. Introducer 12 can be constructed of a variety of metal grade metals known in the art including stainless steel such as 304 or 304V stainless steel as well shape memory metal such as Nitino. Introducer 12 can also be constructed from rigid polymers such as polycarbonate or ABS or resilient polymers including Pebax®, polyurethane, silicones HDPE, LDPE, polyesters and combinations thereof.

In various embodiments, introducer 12 can be rigid, semi-rigid, flexible, articulated and steerable and can contain fiber optics (including illumination and imaging fibers), fluid and gas paths, and sensor and electronic cabling. In an embodiment introducer 12 is sufficiently rigid (e.g. has sufficient column strength) to pierce tissue including bone tissue without significant deflection along it longitudinal axis so as to maintain a longitudinal or other position within a tissue site. In another embodiment, all or portions (e.g. the distal portion) of introducer 12 are sufficiently flexible to pierce tissue, and move in any desired direction through tissue to a desired tissue site 5'. In yet another embodiment, introducer 12 is sufficiently flexible to reverse its direction of travel and move in direction back upon itself.

Figure 3:
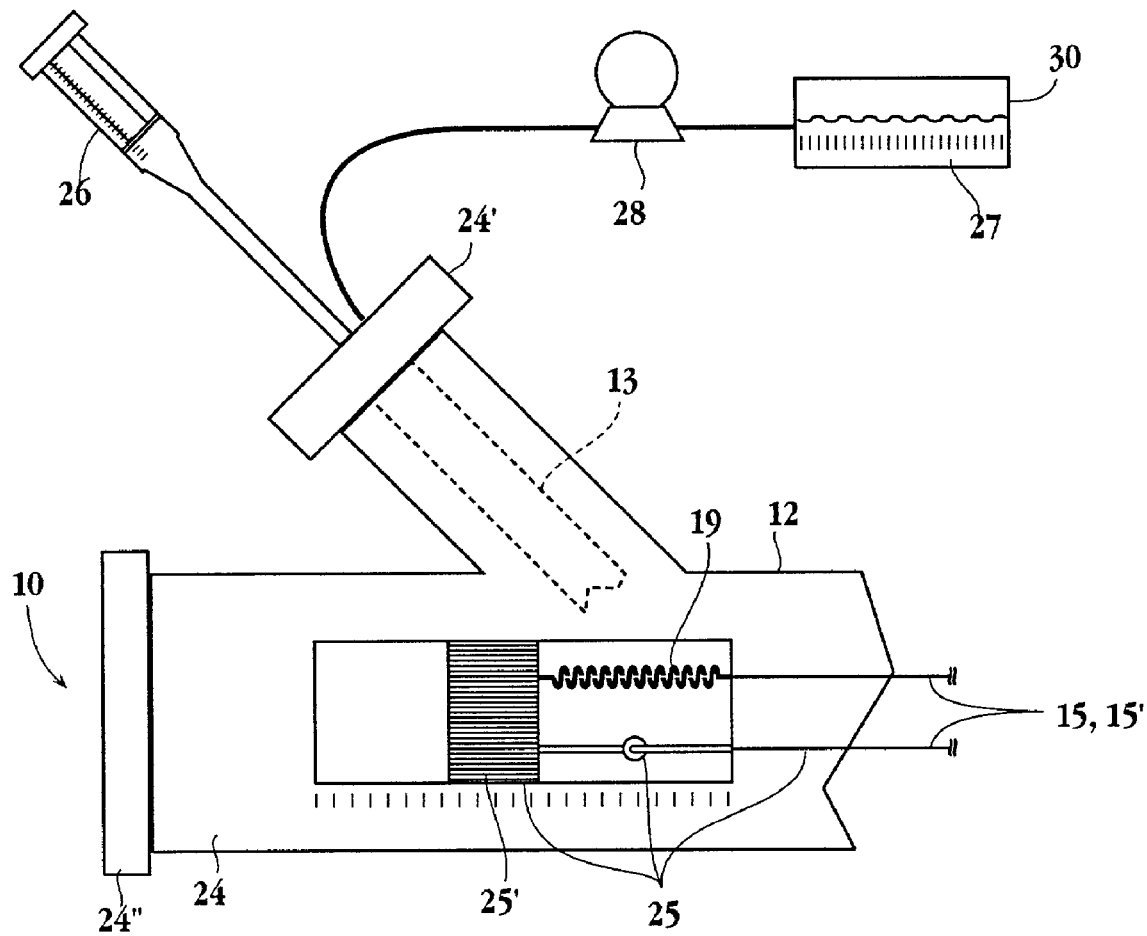
FIG. 3 is a lateral view illustrating various components of the handpiece and associated coupled devices.
Figure 4:
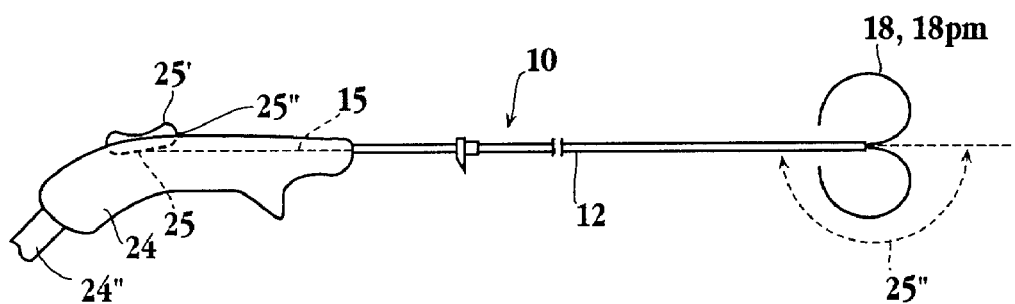
FIG. 4 is a lateral view illustrating an embodiment of the apparatus of FIG. 1 or 2 having a deflectable introducer.

Referring now to FIGS. 3 and 4, in other embodiments all or portions of introducer 12 can be configured to be deflectable and/or steerable using deflection mechanisms 25 which can include pull wires, ratchets, latch and lock mechanisms, piezoelectric materials and other deflection means known in the art. Deflection mechanism 25 can be coupled to or integral with a moveable or slidable actuator 25' on handpiece 24. Mechanism 25 and coupled actuator 25' are configured to allow the physician to selectively control the amount of deflection 25" of distal tip 16' or other portion of introducer 12. Actuator 25' can be configured to both rotate and deflect distal tip 16 by a combination of rotation and longitudinal movement of the actuator. In a preferred embodiment deflection mechanism 25 comprises a pull wire coupled 15 to an actuator 24' on handpiece 24 described herein.

The amount of deflection of introducer 12 is selectable and can be configured to allow the maneuvering of introducer 12 through very tortuous anatomy and negotiate both obtuse or oblique turns in around various and anatomical structures including vasculature, ducts and bone. In specific embodiments, the distal portions of introducer 12 can be configured to deflect 0–180° or more in up to three axes to allow the tip of introducer 12 to have retrograde positioning capability. The deflection can be continuous or indexed to pre-determined amounts selectable on handpiece 24 using an indexed actuator 25'.

Figure 5:
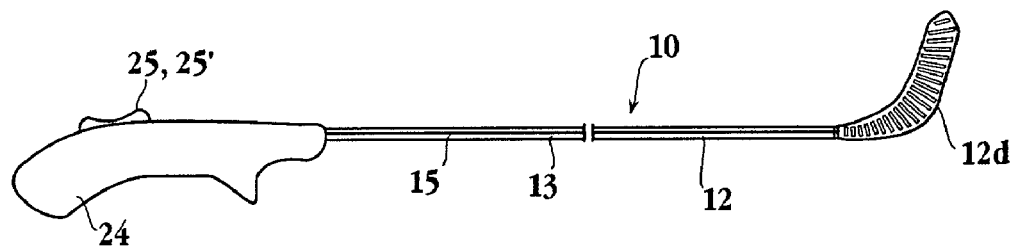
FIG. 5 is a lateral view illustrating an embodiment of the apparatus of FIG. 1 or 2 having a deflectable portion at the distal end of the introducer.
Figure 6:
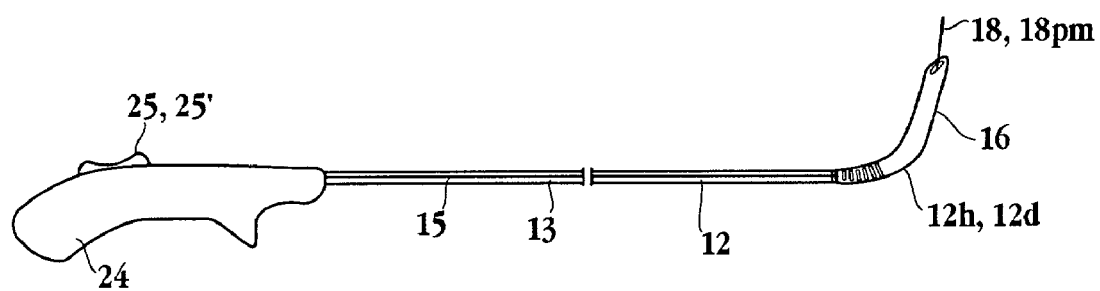
FIG. 6 is a lateral view illustrating an embodiment having a hingedly attached deflectable portion of the introducer.

Referring now to FIGS. 5, 6 (lateral view of an embodiment having deflectable section 12d near the distal end of the introducer) and (lateral view showing a hingedly attached deflectable section), in a specific embodiment introducer 12 has a deflectable or articulated section 12d at or near its distal portion 16. Deflectable portion 12d can be formed by use of corrugated or flexible materials (e.g. materials having a lower durometer than the adjoining less flexible section of the introducer) crimping, sectioning, molding, or other polymer metal working or catheter processing methods known in the art. Deflectable portion 12d can be deflected by a number of means including pull wires, ratchet mechanism, a can mechanism, a gear mechanism (including a rack and pinion or worm gear mechanism) coupled to a pull wire or a stiffening mandrel which is advanced and withdrawn through lumen 13 of the introducer. Deflectable portion 12d can also be hingedly or pivotally attached to introducer 12 using a hinge mechanism which comprise one or more hinged sections 12h actuated by a pull wire or stiffening mandrel 15. Sections 12h can be mechanically coupled to introducer 12 and each other using one or more hinged or pivot joints 12j known in the art.

Figure 7A:
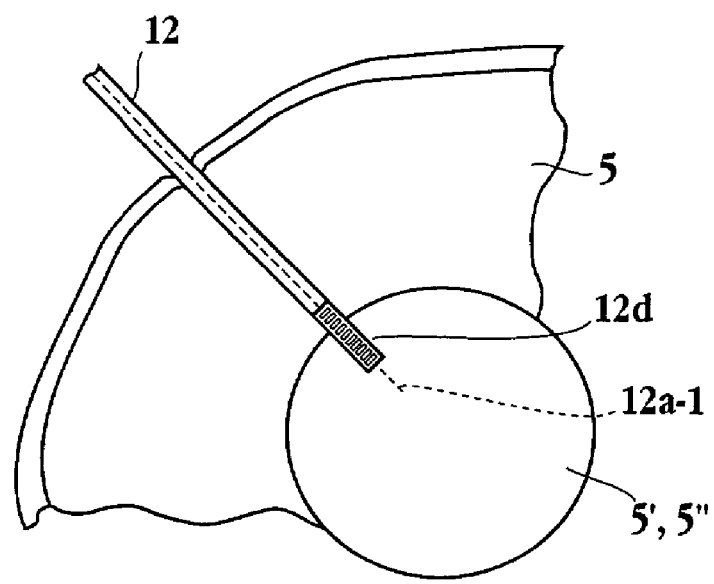
FIGS. 7a and 7b are lateral views illustrating use of an apparatus having a deflectable introducer useful in an embodiment of method the invention.
Figure 7B:
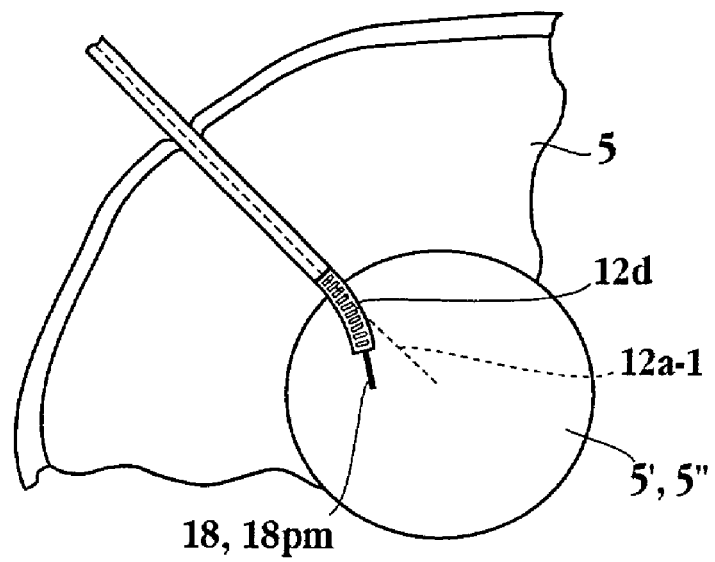
Figure 8A:
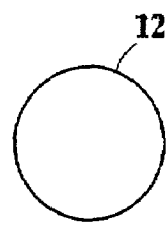
FIGS. 8a–8j are cross sectional views illustrating various cross sectional shapes of the introducer and lumen.
Figure 8B:
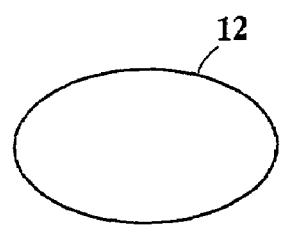
Figure 8C:
Figure 8D:
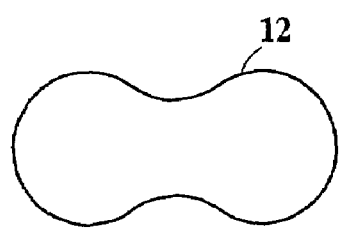
Figure 8E:
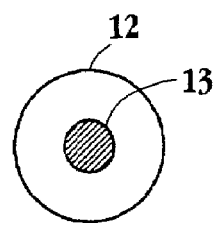
Figure 8F:
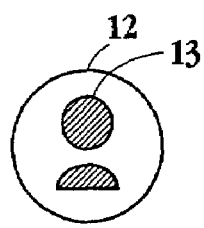
Figure 8G:
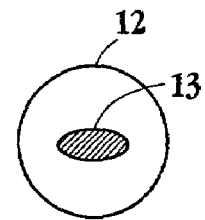
Figure 8H:
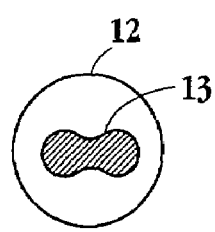
Figure 8I:
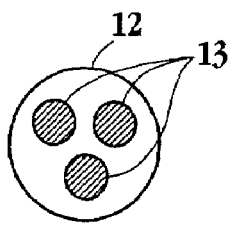
Figure 8J:
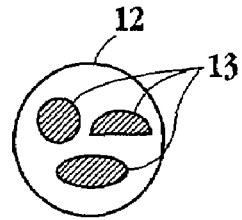
Figure 9A:
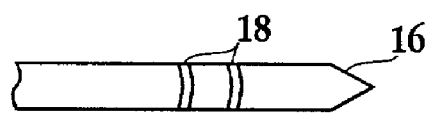
Figure 9B:
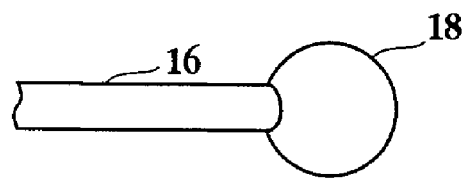
Figure 9C:
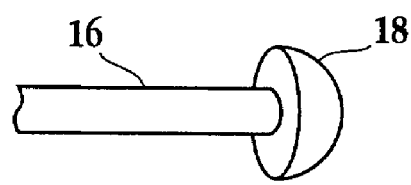
Figure 9D:
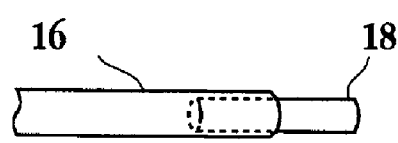
Figure 9E:
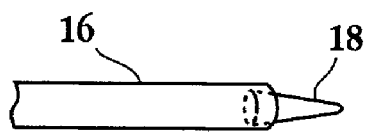
Figure 9F:
Figure 9G:
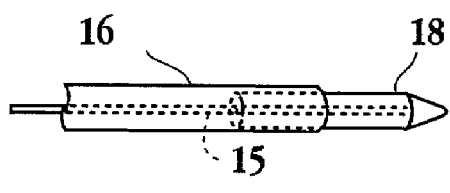
Figure 9H:
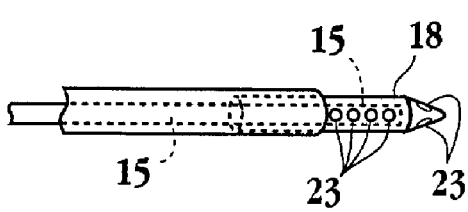

Referring to FIGS. 7a and 7b (perspective views illustrating the use of the deflectable section 12d). In use, deflectable portion 12d allows the introducer to be introduced into tissue site 5' in a first fixed position (preferably straight with respect to a longitudinal axis 12al of the introducer) and then deflected a selectable amount to a second position in order to facilitate deployment of one or more energy delivery devices 18 into tumor mass 5" or tissue site 5'. Further, deflectable portion 12d allows the energy delivery devices to be deployed at a selectable angle (including ranges from acute to oblique) with respect to the longitudinal axis 12al of the introducer. These capabilities provides several benefits including (i) ensuring a more complete deployment of the energy delivery devices into the selected tumor mass; (ii) allowing faster deployment and withdrawal of the energy delivery devices reducing procedure time; (iii) allows the energy delivery device 18 to be positioned and deployed in an irregularly shaped tumor masses (e.g. oblong, oval); (iv) allows the apparatus and energy delivery devices to be positioned and deployed in curved or otherwise difficult to reach portions of the anatomy including the orthopedic anatomy; and (v) allows the apparatus and energy delivery devices to be deployed at tumor site near or adjacent a delicate or sensitive anatomical structure(e.g. the spinal cord, artery) with a reduced or otherwise inappreciable risk of injuring that structure). In alternative embodiments, deflectable portion 12d can also be used to direct the delivery of an infusion fluid (including a jet or stream of fluid) described herein to a selectable portion of the tissue site 5' or tumor mass 5".

In another embodiment introducer 12 can include side ports which allow electrodes 18 to be deployed at a selectable angle with respect to the longitudinal axis 12al of introducer 12, including about 45 and 90°. The use of such side ports is described in U.S. Pat. No. 5,683,384, which is incorporated by reference herein.

Referring to FIG. 8, introducer 12 can have a substantially circular, semicircular, oval or crescent shaped cross section, as well as combinations thereof along its lengths. Similarly, lumens 13 can have a circular, semicircular, oval or crescent shaped cross section for all or a portion of the length 12" of introducer 12.

A variety of energy delivery devices and power sources can be utilized by embodiments of the invention. Specific energy delivery devices 18 and power sources 20 that can be employed in one or more embodiments include, but are not limited to, the following: (i) a microwave power source coupled to a microwave antenna providing microwave energy in the frequency range from about 915 MHz to about 2.45 GHz (ii) a radio-frequency (RF) power source coupled to an RF electrode, (iii) a coherent light source coupled to an optical fiber or light pipe, (iv) an incoherent light source coupled to an optical fiber, (v) a heated fluid coupled to a catheter with a closed or at least partially open lumen configured to receive the heated fluid, (vi) a cooled fluid coupled to a catheter with a closed or at least partially open lumen configured to receive the cooled fluid (viii) a cryogenic fluid, (ix) a resistive heating source coupled to a conductive wire, (x) an ultrasound power source coupled to an ultrasound emitter, wherein the ultrasound power source produces ultrasound energy in the range of about 300 KHZ to about 3 GHz, (xi) and combinations thereof.

For ease of discussion for the remainder of this application, the energy delivery device includes a plurality of RF electrodes 18 and the power source utilized is an RF power supply. For these and related embodiments RF power supply delivers 5 to 200 watts, preferably 5 to 100, and still more preferably 5 to 50 watts of electromagnetic energy isto the electrodes of energy delivery device 18 without impeding out. The electrodes 18 are electrically coupled to energy source 20. The coupling can be direct from energy source 20 to each electrode 18 respectively, or indirect by using a collet, sleeve, connector, cable and the like which couples one or more electrodes to energy source 20. Delivered energies can be in the range of 1 to 100,000 joules, more preferably in the range 100 to 50000 joules, still more preferably in the range of 100 to 5000 and still yet more preferably in the range 100 to 1000 joules. Lower amounts of energy can be delivered for the ablation of smaller structures such as nerves and small tumors with higher amounts of energy for larger tumors. Also delivered energies can be modified (by virtue of the signal modulation and frequency) to ablate or coagulateblood vessels vascularizing the tumor. This provides the benefit of providinga higher degree of assurance of destroying other otherwise occluding the blood supply of the tumor.

Turning now to a discussion of the fabrication and configuration of the RF electrodes, in various embodiments electrode 18 can be made of a variety of conductive materials, both metallic and non-metallic. Suitable materials for electrode 18 include, steel such as 304 stainless steel of hypodermic quality, platinum, gold, silver and alloys and combinations thereof. Also, electrode 18 can be made of conductive solid or hollow straight wires of various shapes such as round, flat, triangular, rectangular, hexagonal, elliptical and the like. In a specific embodiment all or portions of electrodes 18 can be made of a shaped memory metal, such as NiTi, commercially available from Raychem Corporation, Menlo Park, Calif.

Figure 22A:
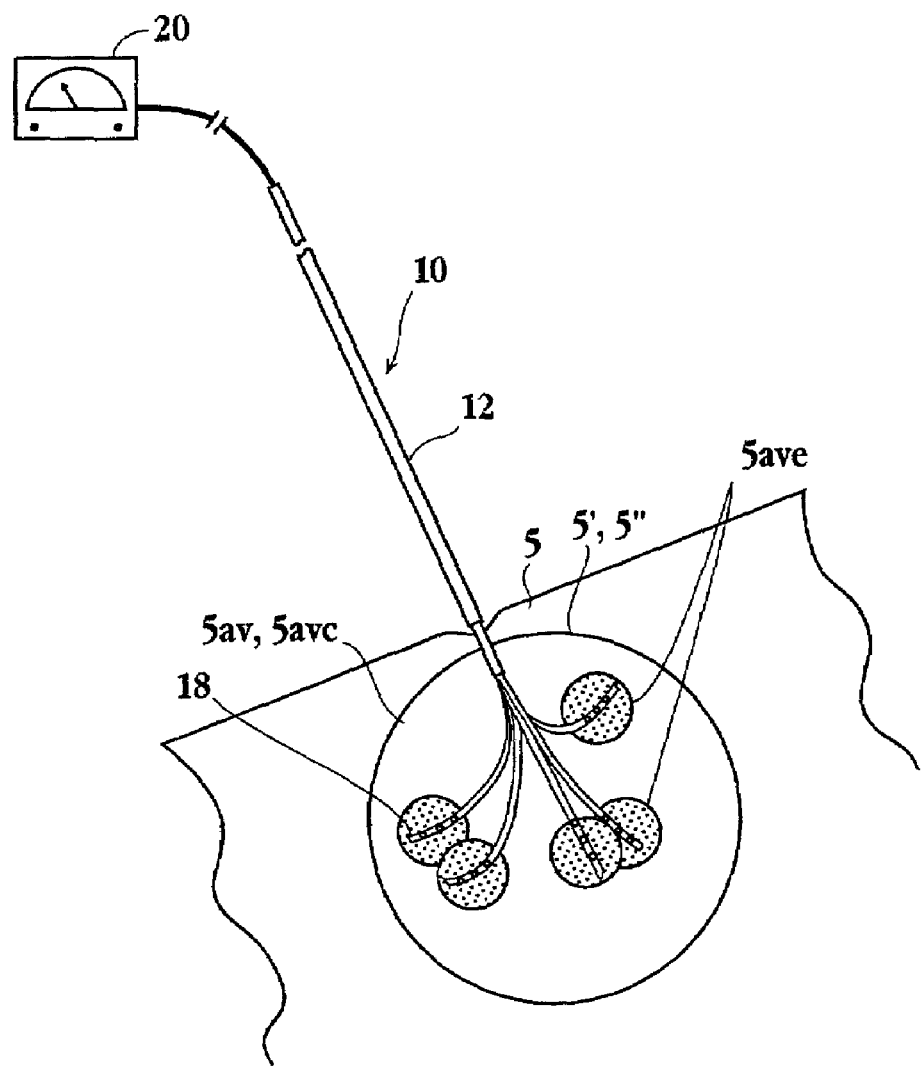
FIGS. 22a and 22b are lateral perspective views illustrating the use of multiple infusing electrodes to generate an ablation volume.
Figure 22B:
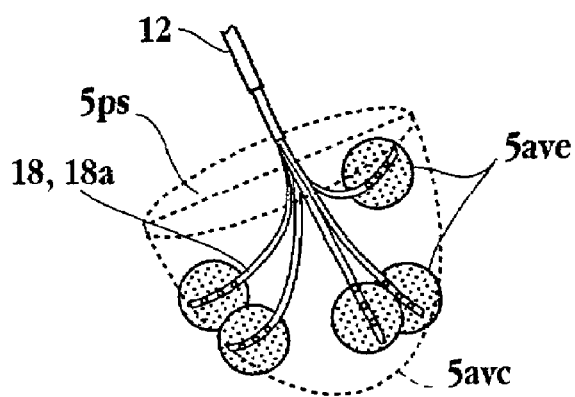
Figures 23, 24:
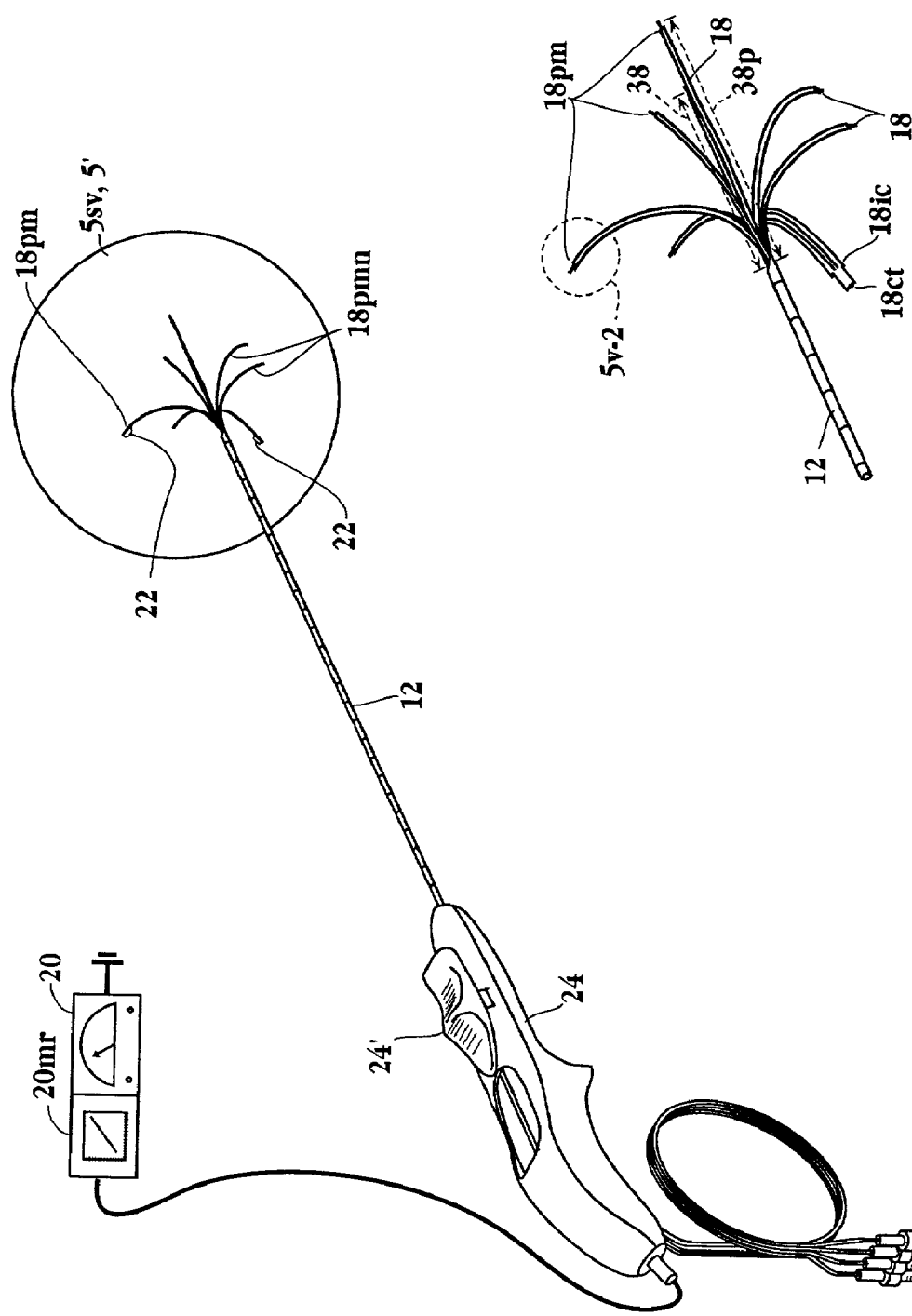
FIG. 23 is a perspective view illustrating an embodiment of a tissue infusion ablation having one or more passive monitoring members and ablation electrodes/active members positionable at a tissue site.
FIG. 24 is a perspective view illustrating various embodiments of positioning of sensors on the passive member and coupling of sensors to monitoring resources.

Referring back to FIGS. 1–2, the plurality electrodes 18 are carried in the device for movement between retracted positions at which the electrodes are disposed within the device's lumen, and deployed positions at which the electrodes are deployed from the distal end, preferably at a plurality of arcuate, laterally extending, angularly spaced positions, as illustrated in FIGS. 2 and 22–24 in particular. By arcuate is meant the electrodes fan out away from the device distal tip in a curved fashion with one or more radii of curvature. By laterally extending is meant that the electrodes in their deployed positions extend radially outwardly away from the device distal tip. By angularly spaced is meant that the electrodes, when viewed from the top as in FIG. 23, are spaced from one another with an angle typicallybetween 20–120 degrees, depending on the number of electrodes in the electrodeset. 'As will be discussed below, each deployed electrode defines an individual-electrode ablation volume, such as a spherical volume, which is proximate to that electrode when an RF current is applied to that electrode, with such deployed in tissue. Also as discussed below, where continued application of RF current (which may be measured as power) to the electrodes causes the individual-electrode ablation volumes to grow and merge with each other to form a combined-electrode ablation volume.

The electrodes are typically ganged together at their proximal ends for movement as a unit between the retracted and deployed positions (which can include partially deployed positions). A handle or other actuator is carried on or otherwise functions with the device to allow the user to move the electrodes from their retracted positions to various deployed (partially or fully deployed) positions. Such electrode construction is known.

Electrodes, such as electrode 18, can include one or more coupled sensors 22 to measure temperature and impedance (both of the electrode and surrounding tissue), voltage and current other physical properties of the electrode and adjacent tissue. Sensors 22 can be positioned on the exterior or interior surfaces of electrodes 18 at their distal ends or intermediate sections. A radiopaque marker 11 can be attached, soldered or coated on electrodes 18 for visualization purposes.

Figure 10:
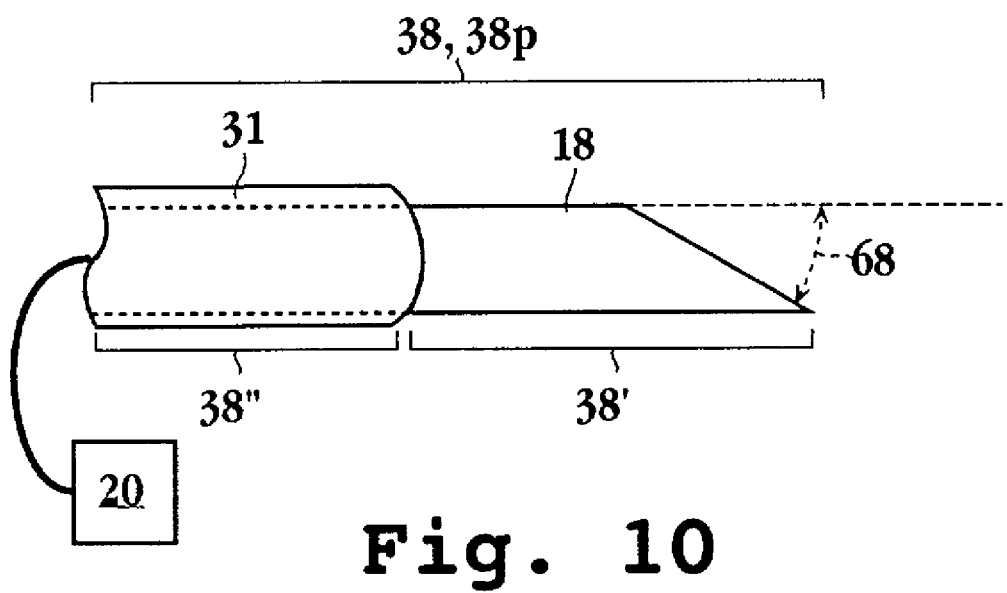
FIG. 10 is lateral view illustrating an embodiment of a needle electrode configured to penetrate tissue.
Figure 11:
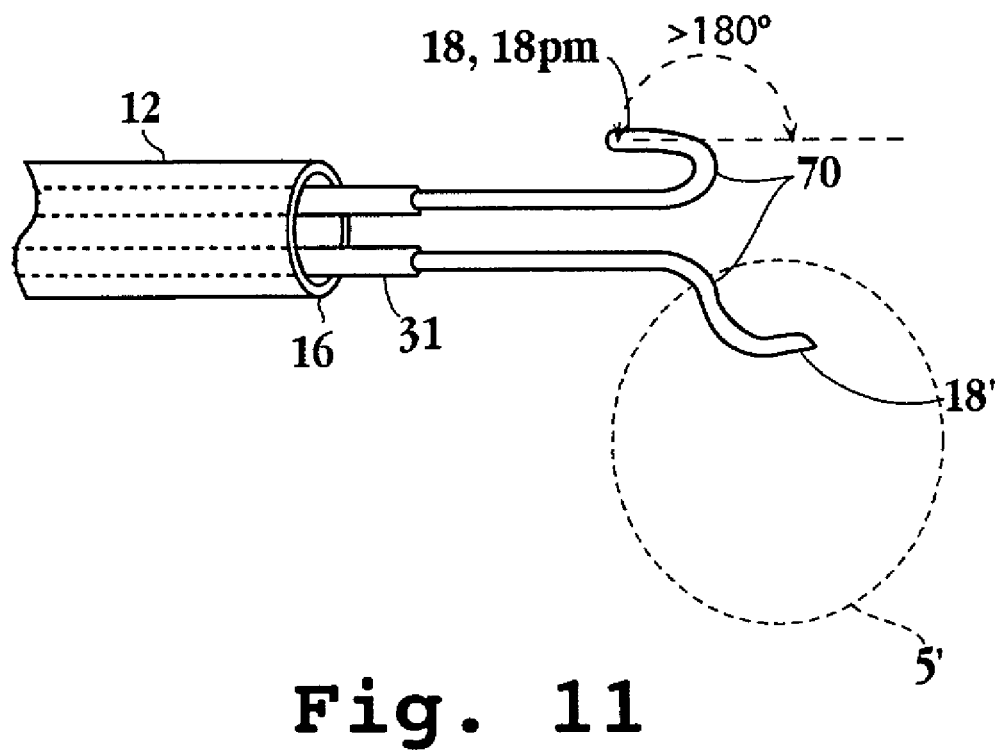
FIG. 11 is lateral view illustrating a needle electrode having at least one radii of curvature.

Referring now to FIGS. 9–11 in various embodiments electrodes 18 can have variety of shapes and geometries including but not limited to ring-like, ball, hemispherical, cylindrical, conical or needle-like as illustrated in FIG. 9. In an embodiment shown in FIG. 10, electrode 18 can be a needle with sufficient sharpness to penetrate tissue including bone, cartilage and fibrous tissue and encapsulated tumors. The distal end of electrode 18 can have a cut angle 68 that ranges from 1 to 60°, with preferred ranges of at least 25° or, at least 30° and specific embodiment of 25° and 30°. The surface electrode 18 can be smooth or textured and concave or convex. The conductive surface area 38' of electrode 18 can range from 0.05 $mm^2$ to 100 $cm^2$. Referring to FIG. 11, electrode 18 can also be configured to be flexible and or deflectable having one or more radii of curvature 70 which can exceed 180° of curvature. In use, electrode 18 can be configured and positioned to heat, necrose or ablate any selected target tissue volume 5'.

Electrode 18 can have selectable lengths 38 that are advanced from distal end 16 of introducer 12. The lengths can be determined by the actual physical length of electrode(s) 18, the length of an energy delivery surface 38' of electrode 18 and the length, 38" of electrode 18 that is covered by an insulator. Suitable lengths 38 include but are not limited to a range from 1–30 cm with specific embodiments of 0.5, 1, 3, 5, 10, 15 and 25.0 cm. The actual lengths of electrode 18 depends on the location of tissue site 5' to be ablated, its distance from the site, its accessibility as well as whether or not the physician chooses a endoscopic, percutaneous, surgical or other procedure.

Figure 12:
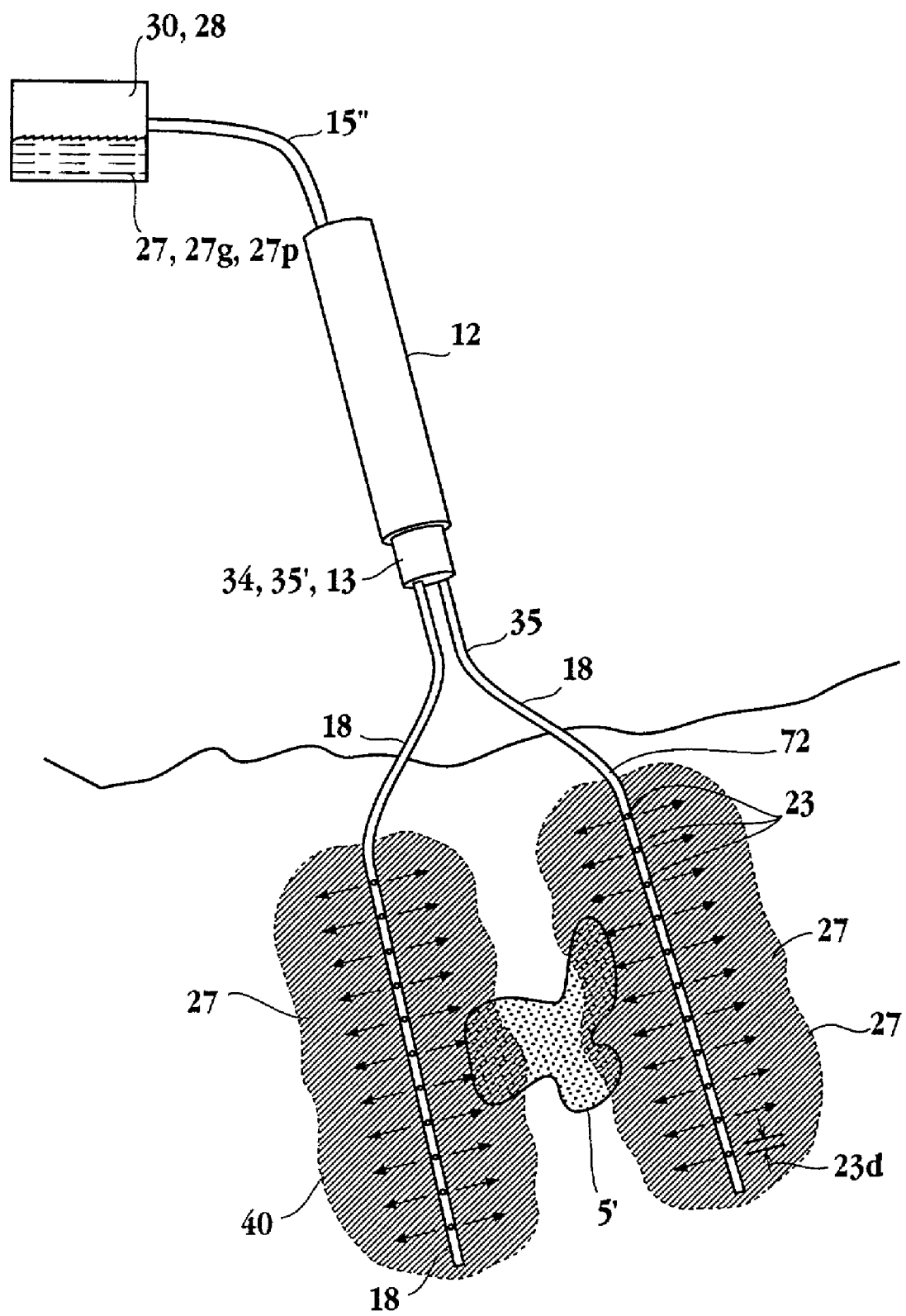
FIG. 12 is a lateral view illustrating an embodiment of an electrode having a lumen and apertures for the delivery of fluid and the use of infused electrolytic fluid to create an enhanced electrode.

Referring now to FIG. 12, in various embodiments electrode 18 can include one or more lumens 72 (which can be contiguous with or the same as lumen 13) coupled to a plurality of fluid distribution ports 23 or apertures 23. Fluid distribution ports 23 can be evenly formed around all or only a portion of electrode 18 and are configured to permit the introduction or infusion of a variety of fluids 27 to a selected tissue site as well to the electrode surface. This can be accomplished by having ports 23 fluidically coupled to lumens 13 (via lumens 72 or fluid channel) that are in turn fluidically coupled to fluid reservoir 30 and/or fluid delivery device 28. Ports 23 can configured to delivery fluids at both low flow rates and Reynolds numbers (e.g. wicking) to high flow rates a (e.g., jetting) and levels there between as well as low and high viscosity fluids with a viscosity range including but not limited to 1 to 100 centipoise with specific embodiments of 1, 3, 5, 10 and 20 centipoise. This can achieved by controlling diameter 23$d$, number and location of ports 23 on one or more electrodes 23.

Suitable fluids 27 that can infused or introduced via ports 23 include but are not limited to liquids, pastes, gels emulsions, conductivity enhancing fluids, electrolytic solutions, saline solutions, cooling fluids, cryogenic fluids, gases, chemotherapeutic agents, medicaments, gene therapy agents, photo-therapeutic agents, contrast agents, infusion media and combinations thereof. Examples of suitable conductive gels are carboxymethylcellulose gels made from aqueous electrolyte solutions such as physiological saline solutions, and the like.

In various embodiments the size and diameter of ports 23 can vary depending upon their position on the electrode as well as the size and shape of the electrode. Preferably at least a portion of apertures 23 are positioned and even more preferably concentrated near the distal ends 18$de$ of electrodes 18. In various embodiments 1 to 10 side apertures 23 are positioned near distal end 18$de$, with specific embodiments of 2, 3 and five apertures. These and related configurations allow for the infusion of an conductivity enhancing solution 27 at a location where current density in around the electrode is greatest, allowing the electrode and tissue adjacent the electrode to carry increased current density without desiccation, charring and appreciable impedance rises causing impedance shut downs of power supply 20. This in turn permits larger and faster ablation volumes to be performed without appreciable risk of impedance shut down. Apertures 23 are also configured to wet the surface 18$s$ of electrode 18 (as is more fully described herein) to cool it, increase conductivity and prevent tissue adhesion and charring.

Figure 13A:
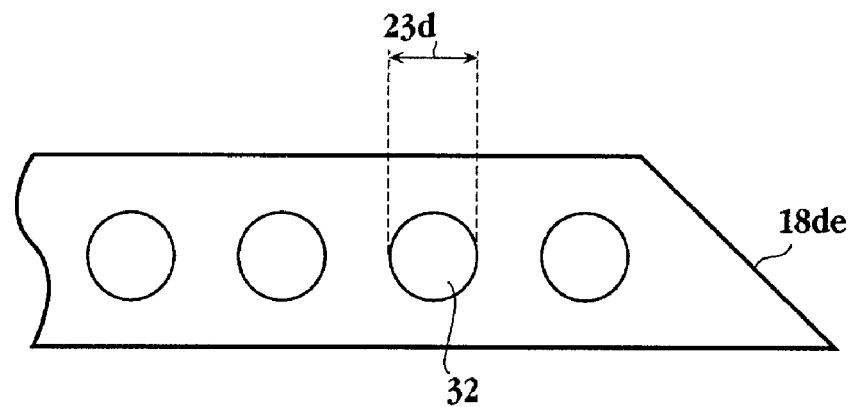
FIG. 13a is a lateral view illustrating an embodiment of an electrode or introducer having apertures with increasing diameters moving in a distal direction.
Figure 13B:
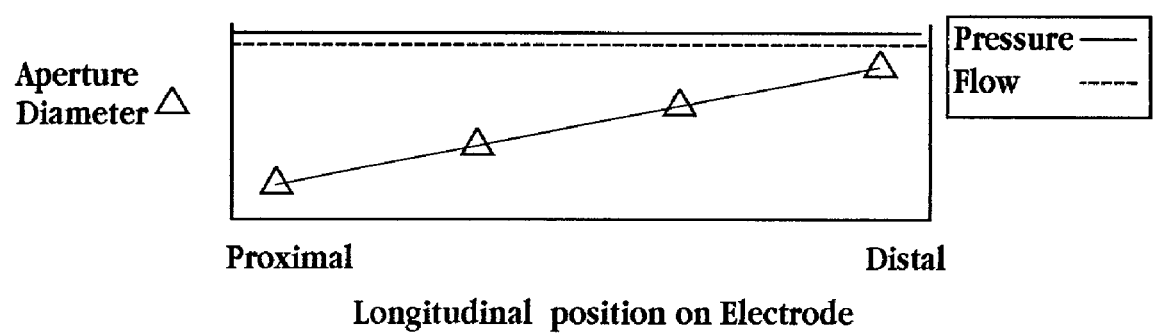
FIG. 13b is a plot showing change in aperture size on progressing toward a needle end.

In an embodiment shown in FIG. 13, ports 23 can be configured to have an increasing diameter 23$d$ moving in a distal direction so as to maintain the flow rate out of each port 23 approximately constant and/or prevent significant decreases due to pressure decreases. The relationship of increasing diameter to distance can linear, parabolic or logarithmic. In an preferred embodiment, the apertures 23 are configured to have increasing diameters going in a distal direction with respect to electrode 18$o$ as to provide a substantially constant flow rate over the apertured portion 18$ap$ of the electrode by decreasing the fluid resistance moving in the distal direction according to Poiseuille's law (F=DP p r 4/8 h l). This is achieved by increasing the aperture diameter 23$d$ about 0.0625% (e.g. about 1:16 ratio) of the increase in lateral distance of placement of the aperture.

Figure 14A:
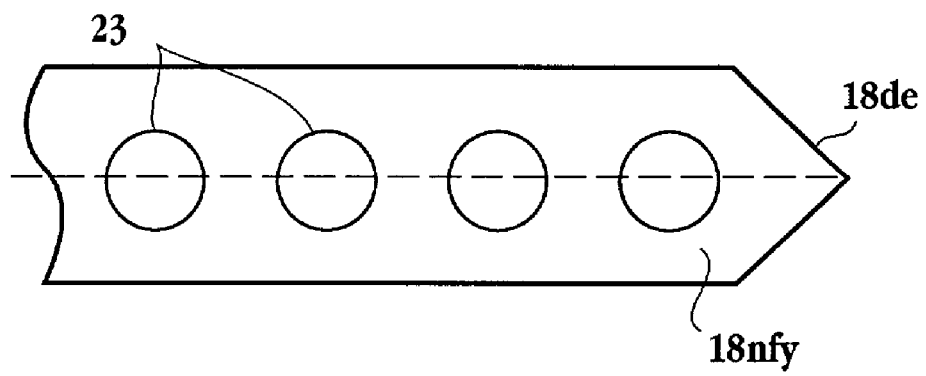
FIG. 14a is a lateral view illustrating an embodiment of an electrode or introducer having one or more apertures positioned on a force neutral axis.
Figure 14B:
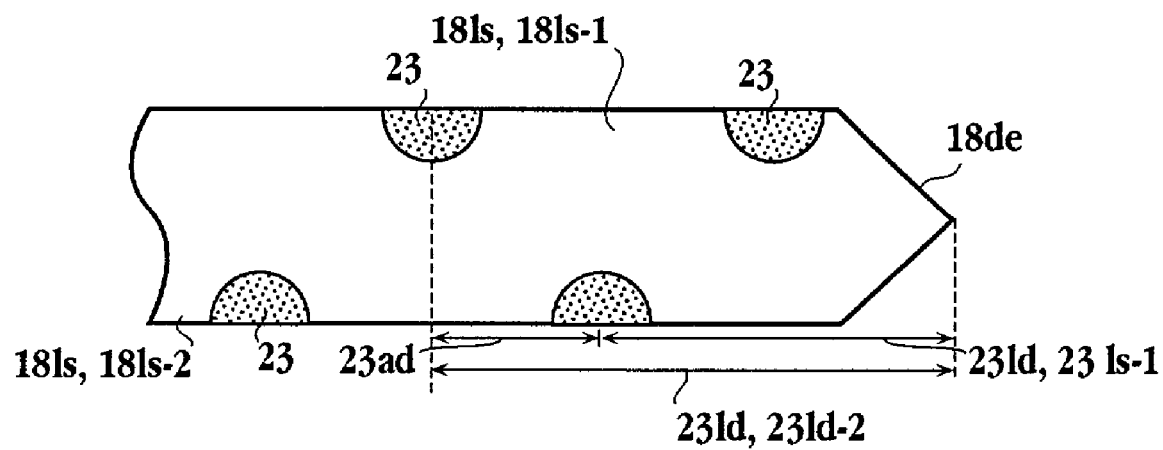
FIG. 14b is a lateral view illustrating an embodiment of an electrode having apertures positioned on opposite lateral sides of the electrode.

Referring now to FIG. 14$a$, in another related embodiment all or a portion of apertures 23 are substantially positioned on a neutral force axis 18$nfa$ of one or more electrodes 18. In these and related embodiments electrodes 18 can be configured to be bendable and/or deflectable. This can be achieved through the selection of the material properties for electrodes as well as its construction and the use off a deflection mechanism described herein. Suitable bendable embodiments of electrodes 18 include electrodes fabricated from spring steel, 304 stainless steel, shape memory metals, nickel titanium alloys (NITINOL), articulated metal, flexible wire, 0.018 flexible wire, high strength polymers, and the like. Positioning apertures 23 along force neutral axis 18$fna$ provides the benefit of an electrode that can deflected or bent omni-directional, without appreciable loss of structural integrity and hence reduced probability of failure. Also the use of apertures 23 infusion holes in electrodes provides the benefit stop crack propagation.

In these and related embodiments apertures 23 can be fabricated using laser drilling or micro-machining or drilling techniques known in the art. The position of force neutral axis 18$nfa$ can be determined from the geometric centerline of electrode 18, calculated using mechanical engineering methods known in the art or identified real time using analytical optical techniques including but not limited to photo-elastic optical methods known in the art including but not limited to moire interferometry, digital speckle pattern interferometry (DSPI) and computer analysis of the fine grid technique. In one embodiment, apertures 23 can be drilled while the optical measurement of lines of stress or strain is being made to obtain a more accurate placement of the apertures along the force neutral line of the electrode. In these and related embodiments drilling of apertures 23 can be facilitated by the use of one or more fixtures known in the art.

In a related embodiment shown in FIG. 14$b$, apertures 23 can also be positioned on opposites lateral sides 18$ls$ of electrodes 18 and offset a distance 23$ad$ to preserve the structural integrity of electrode while reducing the likelihood of plugging on both side of the electrodes. In a specific embodiment one aperture can be positioned 4 mm (distance 23$ld1$) from electrode distal end 18$de$ and second apertures can be positioned on the opposite side of the electrode at distance 6 mm (distance 23$ld2$) from distal end 18$de$.

Figure 15A:
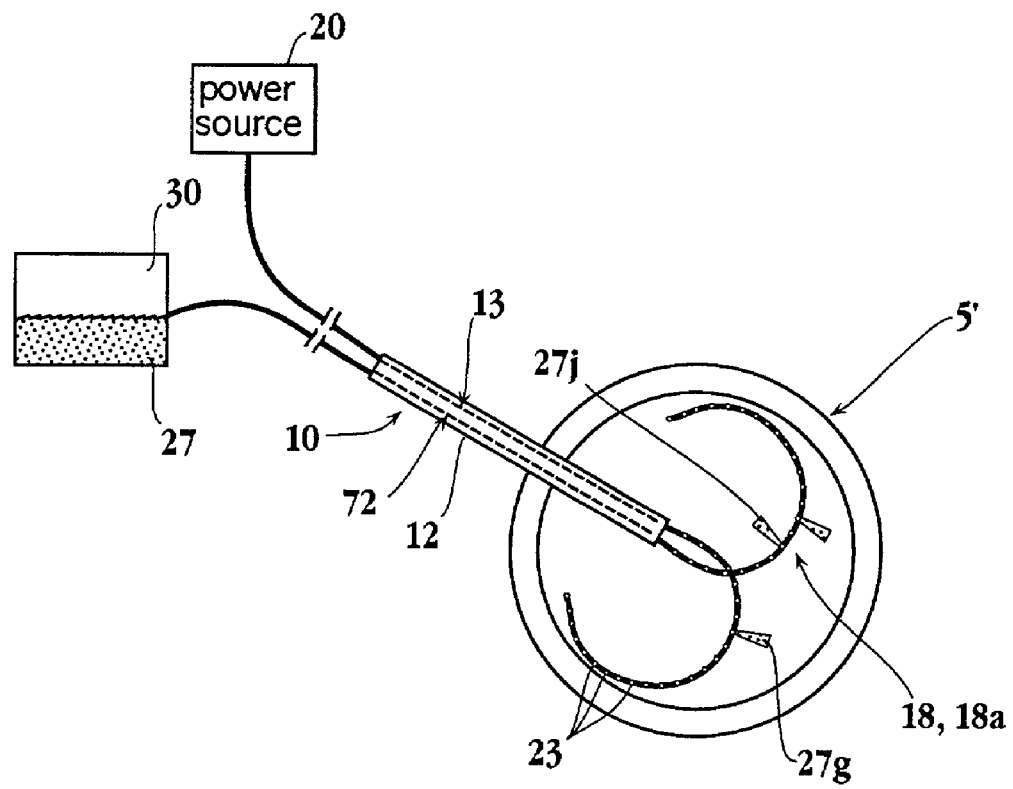
FIG. 15a is a lateral view illustrating an embodiment of an RF electrode with apertures configured to provide a cooling fluid to the electrode and surrounding tissue.
Figure 15B:
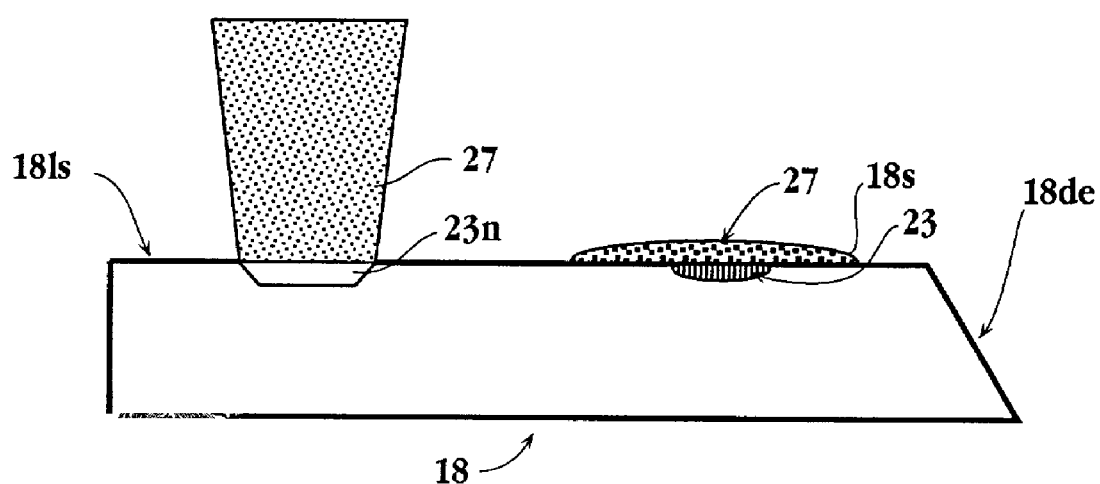
FIG. 15b is an enlarged sectional view showing distribution of infused liquid from different shaped orifices.

In an embodiment shown in FIG. 15, apertures 23 can be configured to provide cooling of one or more electrodes 18 and surrounding tissue to prevent tissue from the development of excessive impedance at electrode 18 from the deposition of charred tissue on the surface of electrode 18. The cooling is accomplished by both the use of a cooled solution to cool the electrodes by convection, conduction and a combination thereof. The amount of cooling can be controlled by control of one or more of the following parameters (i) temperature of the cooling solution (ii) flow rates of the cooling solution (iii) heat capacity (e.g. specific heat) of the cooling solution. Examples of cooling solutions include, water, saline solution and ethanol and combinations thereof. Other embodiments can utilize a cooling fluid or gas 27g which serves to cool electrodes 18 by ebullient cooling or Joule Thomson Effect cooling as well as the mechanisms described above. Embodiments utilizing Joule-Thomson Effect cooling can have a nozzle-shaped aperture 23n to provide for expansion of a cooling fluid 27g. Examples of cooling fluid 27g include, but are not limited to, freon, $CO_2$, and liquid nitrogen.

Referring now to FIGS. 12 and 15, various embodiment apparatus can be configured to infuse or deliver a conductivity enhancing solution 27 or other solution into target tissue site 5' including tissue mass 5". The solution can be infused before during or after the delivery of energy to the tissue site by the energy delivery device. The infusion of a conductivity enhancing solution 27 into the target tissue 5' creates an infused tissue area 5i that has an increased electrical conductivity (verses uninfused tissue) so as to act as an enhanced electrode 40. During RF energy delivery the current densities in enhanced electrode 40 are greatly lowered allowing the delivery of greater amounts of RF power into electrode 40 and target tissue 5' without impedance failures. In use, the infusion of the target tissue site with conductivity enhancing solution provides two important benefits: (i) faster ablation times; and (ii) the creation of larger lesions; both without impedance-related shut downs of the RF power supply. This is due to the fact that the conductivity enhancing solution reduces current densities and prevents desiccation of tissue adjacent the electrode that would otherwise result in increases in tissue impedance. An example of a conductivity enhancing solution includes saline solution, including hypotonic or hypertonic solution. Other examples include halide salt solutions, and colloidal-ferro solutions and colloidal silver solutions. The conductivity of enhanced electrode 40 can be increased by control of the rate and amount of infusion and the use of solutions with greater concentrations of electrolytes (e.g. saline) and hence greater conductivity.

In various embodiments the use of conductivity enhancing solution 27 allows the delivery of up to 2000 watts of power into the tissue site impedance shut down, with specific embodiments of 50, 100, 150, 250, 500, 1000 and 1500 watts achieved by varying the flow, amount and concentration of infusion solution 27. The infusion of solution 27 can be continuous, pulsed or combinations thereof and can be controlled by a feedback control system described herein. In a specific embodiment a bolus of infusion solution 27 is delivered prior to energy delivery followed by a continuous delivery initiated before or during energy delivery with energy delivery device 18 or other means. In another embodiment feedback control is used to prevent impedance rises and failures by monitoring impedance at the electrode-tissue interface and increasing the flow rate of cooling and/or conductive fluid 27 in response to impedance increase using PID or other control algorithms known in the art. In related embodiment feedback control could also incorporate sensor input on the deployed length (e.g. deployment depth) of one or more electrodes and incorporate this into an algorithm to regulate fluid flow, energy delivery power level, duty cycle, duration and other ablation related parameters described herein.

In related embodiments, the conductivity of the tumor mass 5' can be enhanced so as to preferentially increase the rate and total amount of energy delivery of energy to the tumor mass 5' relative to healthy tissue. This can be achieved by infusing solution 27 directly into the tumor mass 5' through the use of a needle electrode 18 placed within the tumor mass only. In related embodiments infusion solution 27 can be configured to remain or be preferentially absorbed or otherwise taken up by tumor mass 5". This can be achieved by controlling by one or more of the osmolality, viscosity and concentration of solution 27.

Embodiments of the invention utilizing infusion of a conductivity enhancing solution 27 provide several important benefits including more consistent and homogeneous ablation volumes as well as faster ablation times. This is achieved by infusing conductivity enhancing solution 27 into the desired ablation volume or target tissue site to both increase and homogenize tissue conductivities throughout the desired ablation volume. This in turn significantly reduces the incidence of tissue desiccation, charring as well as the size zones of higher impedance any of which can slow or prevent the delivery of ablative RF or thermal energy.

Figure 16:
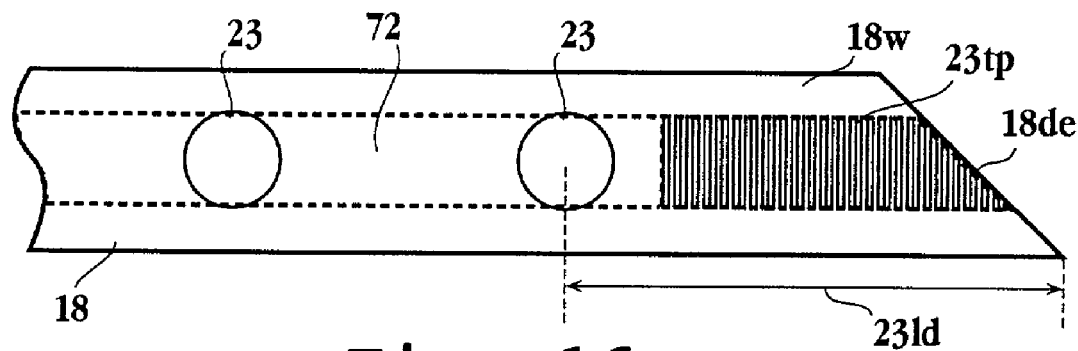
FIG. 16 is a lateral view illustrating an embodiment of the electrode having laterally positioned apertures (e.g. side holes).

Referring now to FIG. 16, in various embodiments all or a portion of infusion ports 23 can be configured as side holes in the wall 18w of electrode 18 offset a minimum longitudinal distance 23ld from the distal tip 18de of electrode 18. These and other embodiments solve the problem of tissue plugging or blocking of fluid delivery lumens 72 which may occur as the electrode is advanced into tissue by position aperture 23 proximally enough such that it is not obstructed by the tissue plug 23tp. Distal end 18de can include an axial aperture 23de or in a preferred embodiment does not to eliminate any tissue coring effect of the electrode. In various embodiments distance 23ld can be in the range of 0.010 to 1 inches, more preferably 0.05 to 0.5 inches and still more preferably 0.1 to 0.25 inches. Specific embodiments can include 0.05, 0.1, 0.15 and 0.16 inches.

Figure 17:
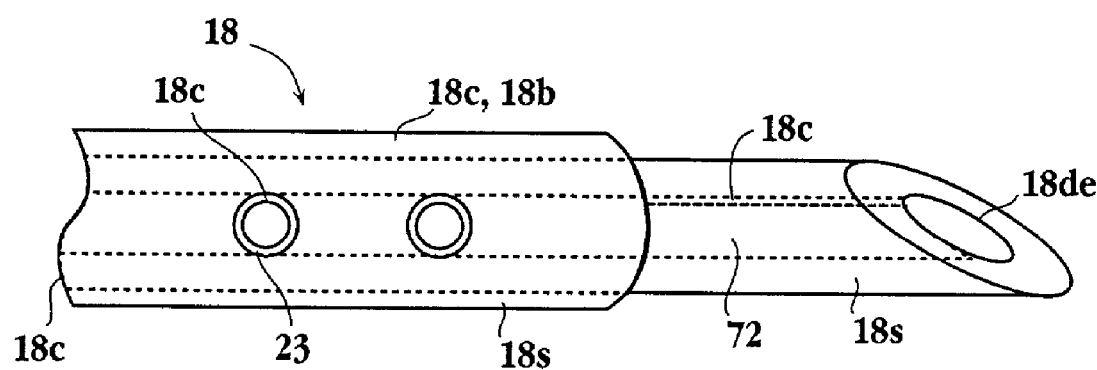
FIG. 17 is a lateral view illustrating an embodiment of the electrode having a non-stick coating to reduce plugging of fluid apertures by adherent and/or coagulated tissue.

In an embodiment shown in FIG. 17, tissue plugging can be overcome through the use of a lubricous or non-stick coating 18c positioned over all or a portion of the surface 18s of electrode 18 including within lumens 72. Coating 18c prevents tissue, including burnt or charred tissue and other biological material from coagulating, adhering or otherwise sticking onto electrode surface 18s, apertures 23 or within lumens 72. In specific embodiments coating 18c is configured to be thermally and/or electrically insulative to prevent any partially adhered tissue from cooking or coagulating onto the surface 18s of electrode 18 reducing the probability of permanent tissue plugging and making partially adherent tissue readily removable by flushing or increase flow rates or pressure of fluid 27. Coating 18c can also be configured to have a sufficiently low surface tension such that tissue and other biological tissue do not stick to it. In various embodiments the surface tension can be below 50 dynes/cm, preferably in the range of 50 to 10 dynes/cm and more preferably in the range 40 to 18 dynes/cm, with specific embodiments of 25, 23, 19, 18.5, 18, 17 and 15 dynes/cm. Suitable coatings 18c can include but are not limited to including, polyamide, polyamide fluoro, PTFE, TEFLON, other fluorocarbon polymers, silicones, paralene and other low surface tension non-stick coatings known in the art. Such coatings can range in thickness 18ct from 0.0001 to 0.1 inches with a preferred embodiment of 0.00 1 to 0.003 inches. Coatings 18c can be applied using co-extrusion dip coating, spray coating, co-extrusion, electro-deposition, plasma coating, lithographic and other coating methods known in the art.

Figure 18A:
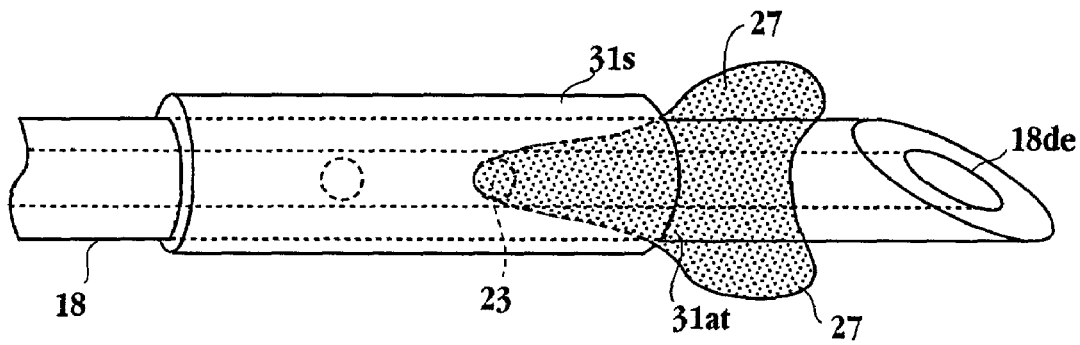
FIGS. 18a–18c are lateral views illustrating use of an embodiment of the electrode having a protective sheath configured to reduce fluid aperture plugging.
Figure 18B:
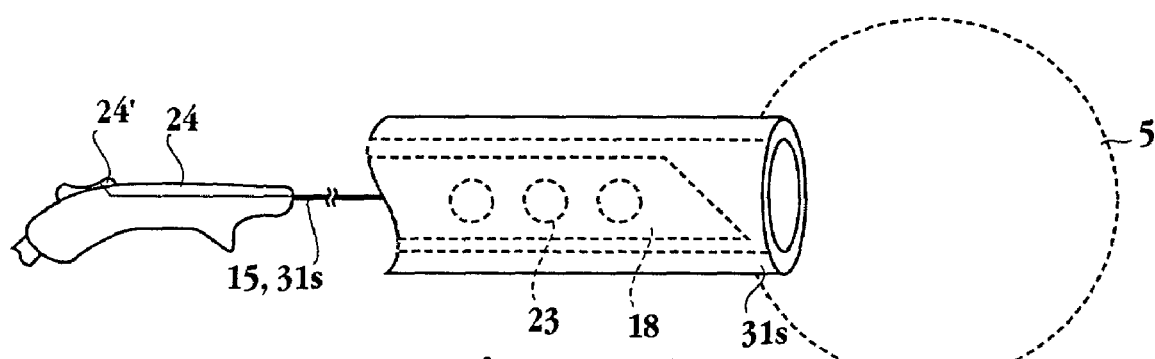
Figure 18C:
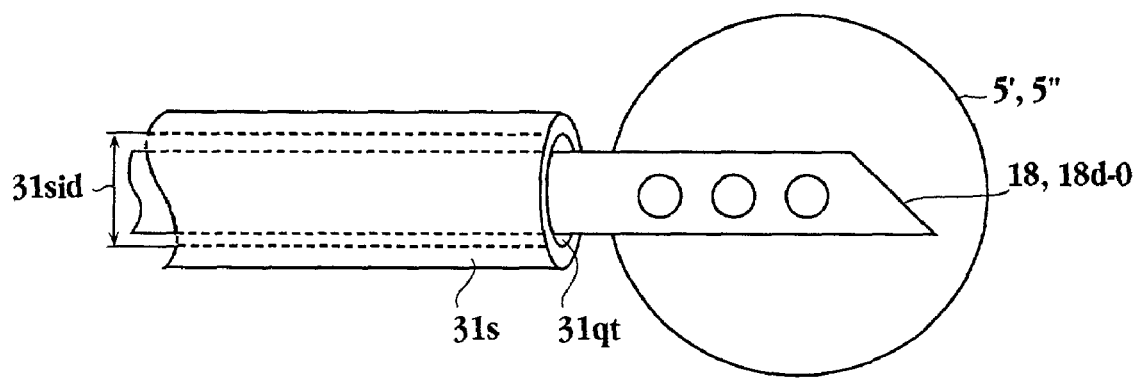

Referring now to FIGS. 18a–18c, in various embodiments electrode 18 can include a fixed or movable sleeve or sheath 31s which covers a selectable portion of apertures 23 preventing them from being blocked or plugged by tissue during either electrode insertion and/or during or after the delivery of RF or other thermally ablative energy. For movable embodiments, sheath 31s can be configured to slide over the outer portion of the electrode or slide through the inner lumen 72 while still not appreciably obstructing fluid flow through the lumen. In an embodiment of a method of the invention sheath 31s can be positioned over all or portion of electrode 18 so as to cover and protect one or more apertures 23 during insertion of electrode into tissue and then subsequently pulled back to allow fluid infusion from uncovered aperture 23 before, during or after the delivery of ablative energy. In a related embodiment sheath 31s can also be configured to be used to control the flow rate of infusion media 27, as well as the total area of electrode 18 available for infusion by uncovering selected segments of apertured electrode 18 which are used for infusion.

Positioning of the slidable sheath 31s can be controlled by configuring the sheath to be directly coupled to an actuator 24" on handpiece 24. In alternative embodiments positioning of sheath 31s can be controlled by the use of a positioning wire, cam, rocker switch, ratchet mechanism, micropositioner, or servomechanism and the like which is mechanically or electrically coupled to the sheath an actuable by an actuator 24" on handpiece 24.

As discussed herein, sheath 31s can be pulled back (e.g. proximally) once electrodes 18 are positioned at the desired tissue site or in an alternative embodiment sheath 31s can have a sufficient inner diameter 31sid to provide enough of an annular channel or thickness 31at to allow fluid 27 to flow out in annular fashion from apertures 23 (either in a proximal or distal direction) to the desired tissue site. In an embodiment sheath 31s can have diameter 1–5 mm greater than of electrode 18 providing an annular channel with a thickness between 0.5 to 2.5 mm Sheath 31s can be actuated at handle 24 by the physician, and its position along electrode 18 is controlled. The sheath 31s can be made from a variety of polymers including, but not limited to resilient polymers, elastomers, polyesters, polyimides, polyurethanes, silicicones, PARALENE, flouropolymers, TEFLON and the like. Also in various embodiments, slidable sheath 31s can be configured to be electrically and/or thermally insulative or can be electrically and thermally conductive using conductive polymers known in the art. An example of a conductive polymer includes Durethane C manufactured by the Mearthane Products Corporation (Cranston, R.I.). Also, all or a portion of the sheath 31s can have radio-opaque, magno-opaque, or echogenic markers to facilitate viewing and placement of the sheath using X-ray, CAT scans, nmr ultrasound and the like.

Figure 19:
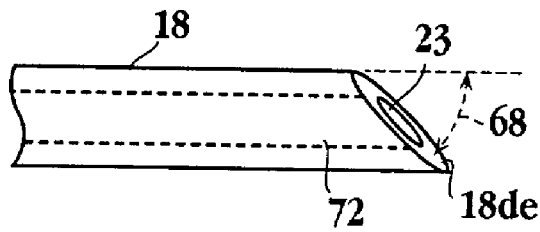
FIG. 19 is a lateral view illustrating an embodiment of the electrode having a bevel angle configured to minimize plugging.

Referring now to FIG. 19, in another embodiment of an electrode configured to reduce plugging of apertures comprises a needle configured to have a needle bevel angle 68 that minimizes tissue coring and hence plugging of lumen 72. In various embodiments the needle angle 68 can be in the range of 5 to 30°, preferably 10 to 20° and still more preferably 12°.

Figure 20A:
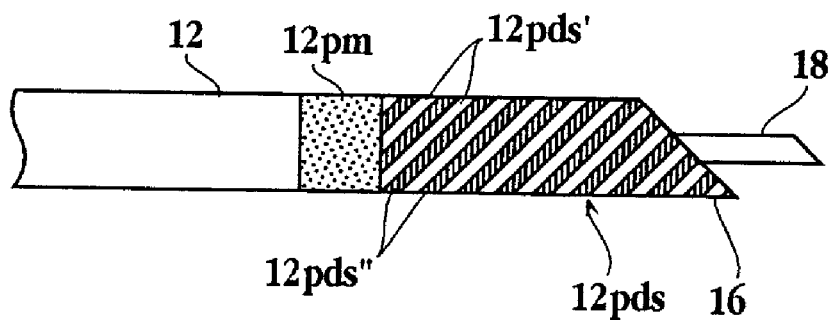
FIGS. 20a and 20b are lateral views illustrating an embodiment of the electrode or trocar having a porous or braided distal portion.
Figure 20B:
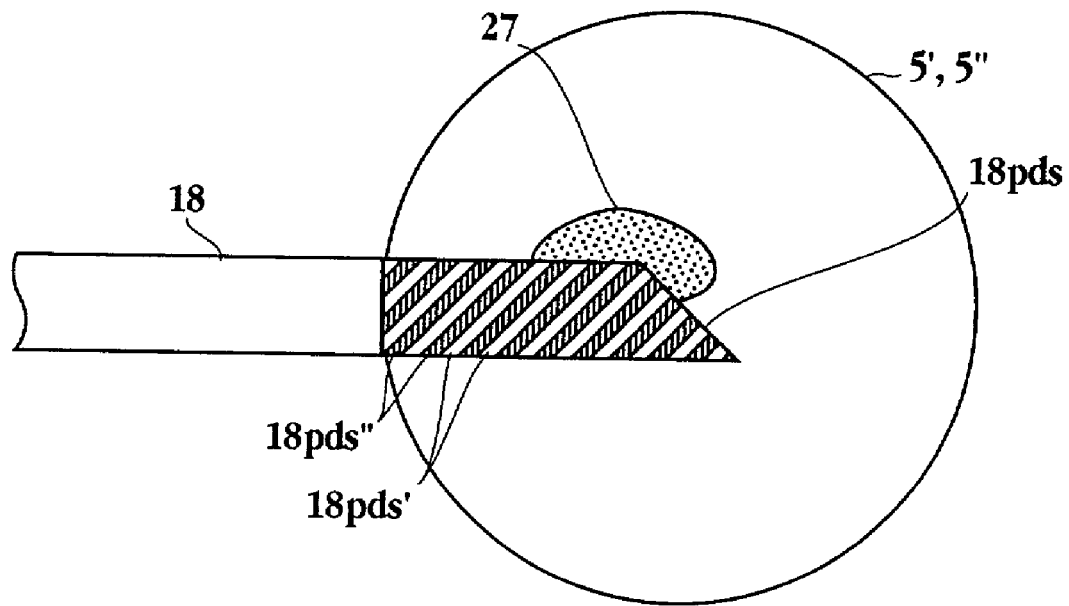

Referring now to FIGS. 20a and 20b, in various embodiments introducer 12 or electrode 18 can include a porous distal section 12pds or 18pds. Porous distal section 12pds or 18pds is configured to allow fluid to diffuse out of the pore and or interstitial spaces 12pds' between braids 12pds". In various embodiments section 12pds can comprise a braided section which has sufficient rigidity or column strength to penetrate tissue, but still porous enough to allow the passage of fluid. Braided section 12pds can be made from braid material known in the art including high strength material and can be wound or woven using methods known in the art including filament winding techniques and carbon fiber filament winding techniques. Suitable braid materials include metal braids such as stainless steel that can be hardened to increase stiffness or high strength polymer braids such as Nylon®, polyester and Kevlar® fibers, examples including Kevlar 29 and Kevlar 49 manufactured by the Dupont Corporation. Other suitable braid materials can include but are not limited to fiberglass, graphite or carbon fibers including Pitch and Pan based carbon fibers. Examples of fiberglass material includes ASTROQUARTZ II, ASTROQUARTZ III and styles 106, 108, 7628 and 7637 manufactured by JPS Industries (Greenville, S.C.). The rigidity of braided or porous section 12pds or 18pds can be achieved through the use of a structural or stiffening member 12sm positionable within all or a portion of porous section 12pds. In various embodiments, member 12sm can be a metal mandrel, such as stainless steel mandrel, a hardened steel mandrel or rigid polymer member made from polycarbonate or other thermoset polymer.

The packing or weave of braids or fibers 12pds or 18pds can be varied to control the fluid porosity of section 12pds that is amount of fluid that diffuses or wicks through the fibers. In various embodiments the porosity of section 12pds can be in the range of 1–2000 cc/min/cm$^2$, preferably in the range of 10 to 1000 cc/min/cm$^2$, with specific embodiments of 20, 50, 100, 250 and 500 cc/min/cm$^2$.

In related embodiments all or portions of sections 12pds or 18pds can be fabricated from heat resistant materials and polymers such that the strength, stiffness or shape of section 12pds or 18pds is not appreciably degraded or altered during the delivery of RF or other thermal ablative energy. Such embodiments solve the problem of softening or deformation of a porous or fluid delivery section 12pds or other section of elongate member 12 that can occur during delivery of thermally ablative energy to a tissue site. Suitable heat resistant polymers and materials include polyetherimide available from the General Electric Company under the trademark ULTEM® and polyetheretherketone available from the General Electric Company under the trademark UNITREX®. In other embodiments all or portions of section 12pds can fabricated from electrically conductive or electrically dissipative polymers. Examples of electrically dissipative polymers include acetals such as UNITAL ESD available from the General Electric Company. In still other embodiments a braided porous section 12pds is configured to increase the surface area for conductive heat transfer from section 12pds and/or energy delivery device 18 to either fluid 27 or the surrounding tissue. These embodiments enhance the heat transfer from energy delivery device 18 and/or section 12pds reducing the likelihood of tissue desiccation and charring on or near the energy delivery device in turn reducing impedance of the energy delivery device and impedance caused shut downs (i.e. called impeding out) of power supply 20.

In another embodiment porous section 12pds including electrode 18 can comprise a porous, microporous or liquid permeable material 12pm fluidically coupled to lumen 13 or 72 and configured to uniformly effuse or diffuse fluid through itself, onto its surface and into tissue. Suitable porous materials include polymer foam, polyester foam, OPCELL foam, ceramic, polyester, polyester membrane, Nylon membrane, glass fiber membranes DACRON, expanded PTFE membranes and porous ceramics known in the art. The pore sizes of porous material 12pm can be in range from 5 to 1000 microns, preferably 40 to 500 microns and more preferably 50 to 150 microns. In these and related embodiments porous section 12pds can be configured to wick, effuse, spray or jet fluid to wet, irrigate and cool the electrode by a combination of one or more of conductive, convective and evaporative cooling. Irrigating the electrodes provides the benefit of preventing and/or reducing an impedance rise at the electrode tissue interface. In embodiment the electrode can be coated with a hydrophilic coating or texture to facilitate wetting of the electrode surface. Examples of hydrophilic surfaces include metal, glass, and plasma treated polymers and metals, whereby the plasma treatment increases the surface tension of the substrate surface via chemical reaction and/or deposition with the surface. The plasma treatment can be a variety of plasma treatment known in the art such as argon plasma treatment.

In an embodiment of a method of the invention, tissue plugging can be prevented or reduced by infusing fluid through one or more electrode lumens 72 when the electrode is inserted into tissue and/or during the delivery of RF or other thermally ablative energy. In various embodiments the infusion rate can be in the range between 0.1 to 2 ml with specific embodiments of 0.2, 0.5, 1.0 and 1.5 ml/min. Tissue infusion flow via a fluid delivery device 28 such as an infusion or syringe pump can be initiated before or during insertion of apparatus 10 into tissue, or before or during deployment of needles 18 into tissue. Also in a related embodiment flow to one or more electrodes 18 can be monitored using sensors 22 to detect developing plugs and using feedback control (described herein) can be increased or otherwise modified to push out the plug or otherwise prevent plug formation. In specific embodiments feedback control can used to initiate a pressure or flow pulse or a series of pulses or related waveforms by the fluid delivery device (e.g. square waves, sinusoidal, step function etc) to push out a developing or existing plug. The pressure pulse can be in the range of 0.05 to 5 atm, preferably 0.1 to 2 atm and still more preferably 0.3 to 1 atm.

Turning now to a discussion of the use of infusion with RF energy delivery, while such a combination present advantages during ablative treatment there are also technical challenges as well. Two such challenges are (i) inconstant flow and (ii) inability to achieve a homogenous level of infusion, and or inability to infuse the entire volume of a target tissue volume particularly with only one infusion port or channel of infusion. Referring now to FIGS. 1–2 and 12–15, various embodiments of the invention solve these problems by providing an apparatus configured to infuse fluid through multiple electrodes 18 or other infusion channels so as to collectively define a larger, more predictable and homogenous or complete infusion volume than would be possible by infusing from a single electrode 18 or channel. Such embodiments solve the problem of inconstant flow or incomplete, uneven or otherwise non-homogenous ablation volumes that may result without infusion or with only a single infusion channel. Uneven ablations can occur with a single infusion channel due to uneven or incomplete infusion volumes and/or zones within the desired infusion volume receiving differing amounts of infusion fluid.

In various embodiments feedback control described herein can also be employed to improve the uniformity of infusion volumes as well as better control the infusion process. This can be achieved by utilizing feedback control to monitor and control flow rates through each electrode 18 or infusion channels 72 to compensate for flow variation in any one channel and ensure more uniform volume of infusion and subsequent ablation volumes. Embodiments of the invention configured to infuse through multiple electrodes provide the advantage of reducing collective back pressure that results from a single infusion channel from fluidic pressure at the target tissue site 5" due to tissue resistance, obstruction or plugging of a single electrode. Consequently, by distributing infusion over multiple electrodes and multiple apertures at multiple site overall flow rates, infusion rates and infusion volumes can be increased and more uniform infusion can be achieved for a selected target tissue site than via use of a single point of infusion. In particular, by controlling infusion of liquid to the individual electrodes, liquid can be supplied through each electrode at a desired flow rate, independent of the resistance to flow of other individual electrodes, allowing, for example, equal flow rates to be applied to the electrodes.

Figure 21:
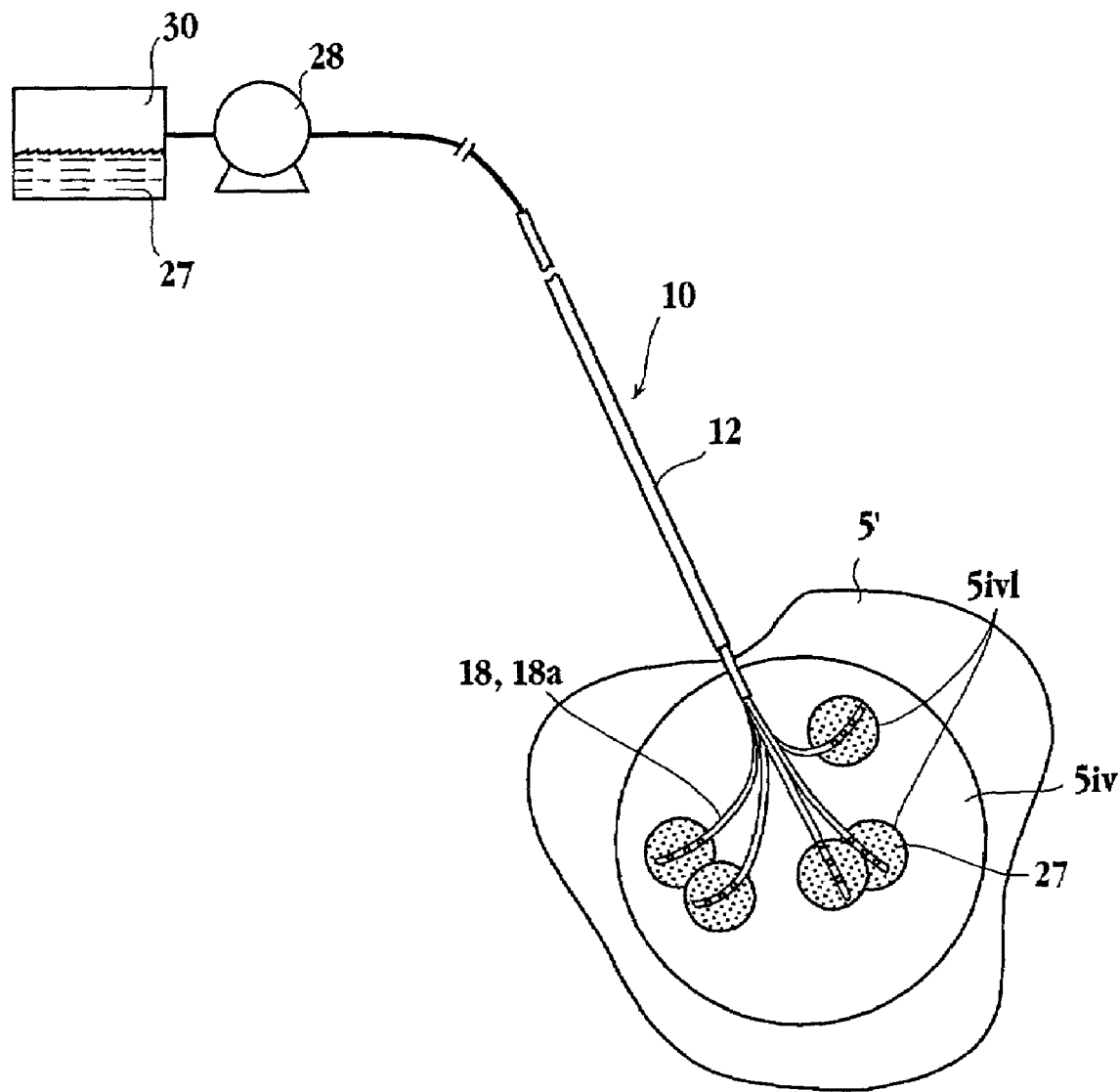
FIG. 21 is a lateral view illustrating an embodiment of a method of the invention in which fluid is infused through multiple electrodes to create infusion zones that coalesce to form a larger infusion volume.

Referring now to FIG. 21, in an embodiment of a method of the invention fluid is infused through one or more electrodes 18 or infusion channels such that the individual volumes or zones of local tissue infusion $5iv'$ surrounding each electrode grow or coalesce to form one large infusion volume $5iv$. This can be achieved by controlling the flow rate through the electrodes or infusion channels and monitoring the amount infused analytically or visually. The progression of the growth of the infusion volume $5iv$ can be monitored using imaging methods including but not limited to ultrasound, CT scan, MRI, and x-ray. In various embodiments of methods of the invention, the monitoring process can be facilitated by the use of X-ray or flouroscopic contrast agents, echogenic contrast agents, or MRI contrast agents known in the art which are added to infusion media 27. The delivery of ablative energy can be initiated before during or after the completion of the infusion process. In one embodiment, the delivery of ablative energy such as RF energy is initiated only after the collective large infusion volume has formed or substantially about the same time. In another embodiment the delivery of RF energy is initiated before infusion, at it onset or as the local infusion volumes are growing.

In alternative embodiments the delivery of an infusing solution 27 can be enhanced by several means. In one embodiment, ultrasound energy can be delivered to the selected target tissue site 5" during or post infusion to increase the diffusion and permeation of fluid 27 into tissue site 5" including the interstitial space of tissue site 5' via a combination of fluid sonication, agitation (fluid and tissue and/or brownian motion, this analogous to shaking up a bottle containing a dissolvable solid in a liquid to get the solid to dissolve. Further the energy can be configured to cause cell lysis, enabling fluid 27 to diffuse into cells. The ultrasound energy can be delivered by a piezoelectric transducer known in the art that is coupled to one or more electrodes or to a separate catheter/probe in turn coupled to an ultrasound energy source. In various embodiments ultrasound energy can be delivered in the frequency range from 0.5 to 30 MHz, more preferably from 1 to 10 MHz, with specific embodiments of 2, 3, 5 and 8 Mhz.

In another embodiment fluid delivery device 28 can be configured to produce pressure pulses in flow and/or pulsed flow to enhance diffusion. Still another embodiment employs the use of RF or DC voltage to create an electroporation effect known in the art. The DC voltage can be delivered by a separate probe coupled to a DC power source with a voltage known in the art to produce an electroporation affect. Such a voltage source can be in the range of 0.1 to 10 volts.

Referring now to FIG. 22, during the delivery of RF each RF electrode 18 is configured to generate an ablation volume $5ave$ proximate each electrode 18. This volume, which may be spherical or columnar, depending on the length of active region(s) is also referred to herein as an individual-electrode ablation volume, and corresponds to the ablation volume produced by applying an RF current (RF power) to that electrode during the initial phase of RF ablation. When multiple electrode are used, and optionally, electrolyte solution is infused into tissue from the electrodes, application of RF energy to the multiple ablation volumes, e.g., spherical ablation volumes, will result in each ablation volume expanding and eventually merging and overlapping to form a single combined-electrode ablation volume 5avc, also referred to herein as a meta volume.

Depending on the size and shape of the of the desired combined-electrode ablation volume 5av, different number of electrodes 18 can be used to create the meta ablation volume 5avce whose shape a volume approximates that of the desired ablation volume. In various embodiments a range of 2–12, typically 3–10, electrodes are employed to create a corresponding number of individual-electrode ablation volumes. In a specific embodiments four electrodes used to create four ablation volumes 5ave which can have an approximately a tetrahedral orientation.

In a related embodiment platonic solids 5ps (described herein) can be used as a positioning geometric template for individual electrode ablation volumes 5ave to create the desired collective or meta ablation volume size 5avc using the fewest number of individual ablation volumes 5ave. In a specific embodiment each individual electrode ablation volumes 5ave is positioned such that it is bisected by a single face or surface 5pf of the respective platonic solid, with one ablation volume 5ave positioned as such on all faces of the chosen platonic solid. Examples of suitable platonic solids include, but are not limited to a cube, tetrahedron and dodecahedron, as discussed below.

In accordance with one aspect of the invention, the progression of the ablation volumes 5av is monitored using one or more passive (non ablating) sensor elements. Referring now to FIG. 23, apparatus 10 includes one or more passive (non ablating) sensor elements or monitoring members 18pm advanceable from device 12 and positionable within a target tissue site 5' concurrently or independently of the positioning of electrodes 18. As will be appreciated, the sensor elements are carried on the delivery device for movement with respect therein between retracted positions, in which the sensor elements are carried within the lumen of the device, and deployed (including partially deployed) positions in which the sensor elements (or at least their distal ends) are deployed outside of and away from the distal end of the delivery device.

Typically, the sensor elements, when deployed, are arrayed in an arcuate, laterally extending, angularly spaced configuration, with the sensor elements being positioned within the volume corresponding to the combined-electrode ablation volume, and with the individual sensor elements being disposed between adjacent electrodes, as detailed below. Specifically, the sensor elements are typically arrayed outside of the individual-electrode ablation volume in the region of coalescence of ablation volumes of two adjacent electrodes. In this configuration, in the early phases of RF ablation, the sensor elements are located outside of the individual-electrode ablation volumes. As the individual volumes expand and begin to coalesce, the regions of ablation begin to overlap with the sensor elements positions. By placing the sensor elements outside of the initial ablation volumes, the spread of the ablation volume, and ultimately, the desired extent of ablation throughout the combined-electrode ablation volume can be monitored and controlled, as detailed herein.

As will be appreciated, the plural sensor elements may be ganged together for movement as a unit between retracted and deployed positions, as described above for the electrodes, or they may be individually movable to place the sensor elements at different extended positions in the combined-electrode ablation volume. When ganged together, the sensor elements and electrodes and be moved independently of one another or moved as a combined electrode/sensor unit between retracted and deployed positions.

The sensor elements are designed to sense tissue properties rather than deliver ablative energy and accordingly can include one or more sensors 22 or alternatively, all or portion of passive members can be sensing elements 22. Preferably members 18pm are configured to be non conductive and/or to not delivery appreciable amounts of RF or other electromagnetic energy. In various embodiments this can be accomplished by coating all or portions of members 18m with an electrically insulative coating or layer 18ic that can also be thermally insulative as well. Suitable insulative coatings 18ic include, but are not limited to insulative polymers, PARALENE, polyimide, polyamide, TEFLON, NYLON, flouropolymers and other high dielectric materials and insulators known in the art. The coating can be applied using spray coating, dip-coating methods known in the art to produce a uniform coating thickness and consistency. The use of higher dielectric strength materials provides the benefit of thinner coatings which reduces the diameter of passive elements 18mp in turn providing the benefit of making members 18mp more flexible or maneuverable as well as allowing for the positioning and deployment of a greater number of members 18mp from introducer 12. In various embodiments the thickness 18ict of coating 18ic can be in the range of 0.001 to 0.006 inches with specific embodiments of 0.002 and 0.003 inches.

Alternatively, all or portions of passive members 18pm can be fabricated from nonconductive materials such as resilient polymers tubing including not limited to polyethylene, PEBAX, polyimide and other polymers known in the catheter arts.

Passive members 18pm can be made of similar materials and/or have similar properties to electrodes 18, e.g. tissue penetrating ends, bendability, resiliency, memory, spring memory etc which enable members 18pm to be deployed from introducer 12 and positioned at selectable locations within a target tissue site 5" with the exceptions that members 18pm are configured either to not be conductive and or not deliver ablative amounts of RF or other electromagnetic energy. In an embodiment passive member can made from 304v steel or spring steel which has an insulative coating 18ic and also includes a lumen 72 for the passage of both fluids 27 and also electrical wires 15 for coupling to sensors 22.

Referring now to FIG. 24, sensors 22 can be positioned in one or more locations along the length of one or more members 18pm. Also in various embodiments, sensors 22 can be positioned on or flush with the surface of members 18pm, in the interior of members 18pm including within lumens 72 or can be integral to members 18pm including the wall 18pmw of member 18pm. Further sensor 22 can positioned using soldering or adhesive bonding methods known in the medical device arts. Sensors 22 can be electrically coupled directly to members 18pm (whereby an insulted conductive member 18mp provides an electrically coupling of the sensor to monitoring resources describe herein) or can be electrically coupled to one or more insulated wires 15 positioned within lumens 72 and electrically coupled to sensing resources. Suitable sensors 22 for use with members 18pm include but are not limited to temperature, chemical, optical and other sensors described herein.

In embodiment sensors 22 and/or passive members 18pm can be coupled to monitoring resources 20mr directly or via a multiplexing device allowing selective polling and signaling of one or more selected passive elements 18*pm* and or sensors 22. In various embodiments, monitoring resources 20*mr* can comprise monitoring circuitry such as temperature or impedance monitoring circuitry or a monitoring unit 20*mu* comprising monitoring circuitry, a microprocessor/controller, a visual display known in the art and alarm circuitry. In an embodiment, the monitoring unit 20*mu* can be integral to or otherwise electronically or optically coupled to power source 20.

Figure 25:
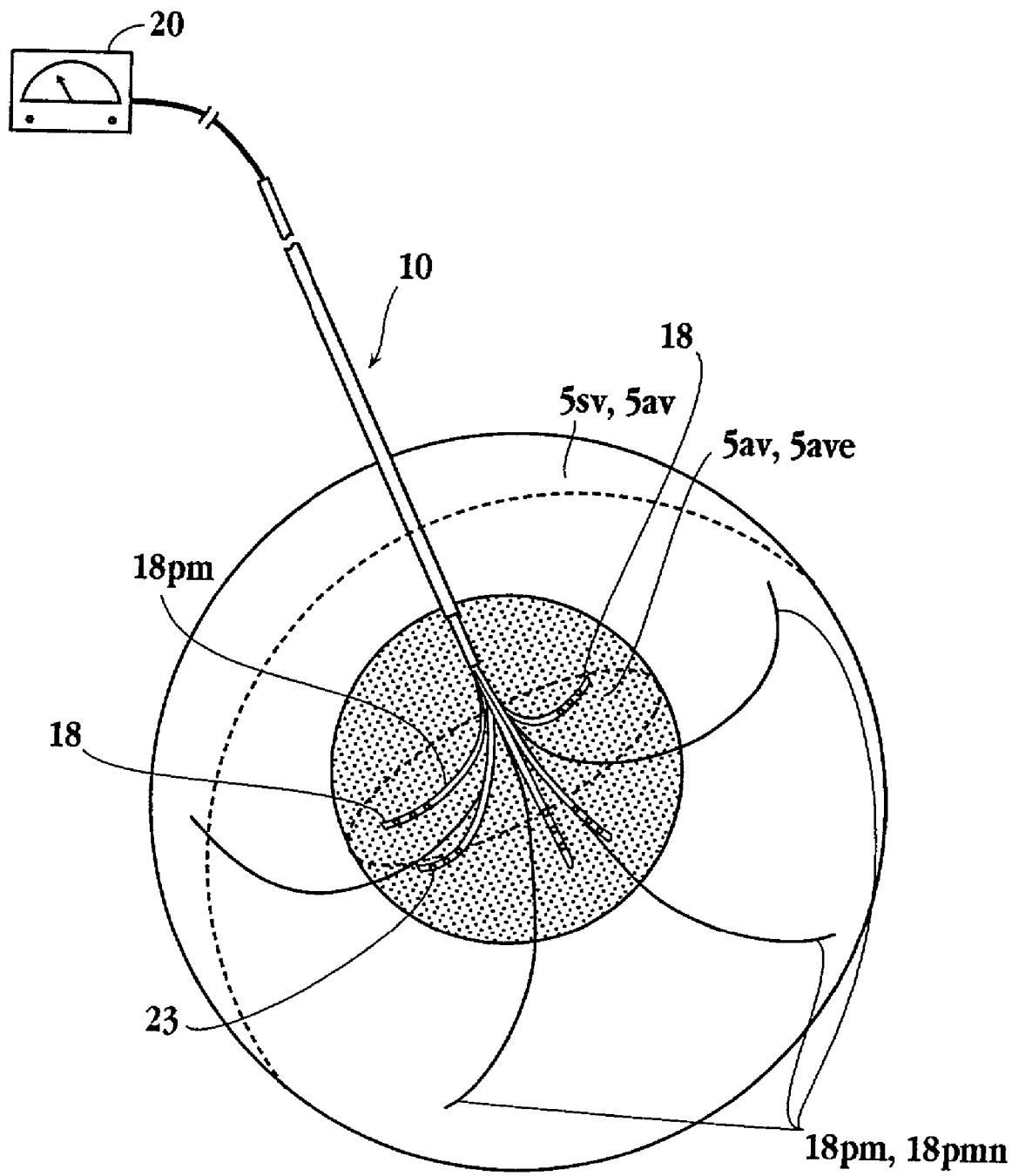
FIG. 25 is a perspective view illustrating the position of passive members to define a sampling volume.

Referring now to FIG. 25, in an embodiment the plurality 20*pmp* of passive members 18*pm* can be positioned to define a sampling volume 5*sv* either by circumscribing the volume and/or positioning within the interior of the sampling volume. Passive members can be manipulated to increase, decrease or change the shape of sample volume 5*sv* being monitored. In various embodiments sample volume 5*sv* can include all or a portion of ablation volume 5*av*, can larger than the ablation volume so as to include all or portion of the ablation volume, define substantially the same volume as ablation volume 5*sv* or be smaller than ablation volume 5*av* to be completely or partially bounded by ablation volume 5*av*. In a related embodiment volume 5*sv* can be configured or manipulated to be substantially separate or distinct from the ablation volume 5*av*. Passive members can be manipulate to define sample volumes having a variety of geometric shapes including but not limited to substantially spherical, hemispherical, oval, pyramidal, tetrahdreral, rectangular, pentagonal, hexagonal, or another selectable platonic solid.

Figure 26:
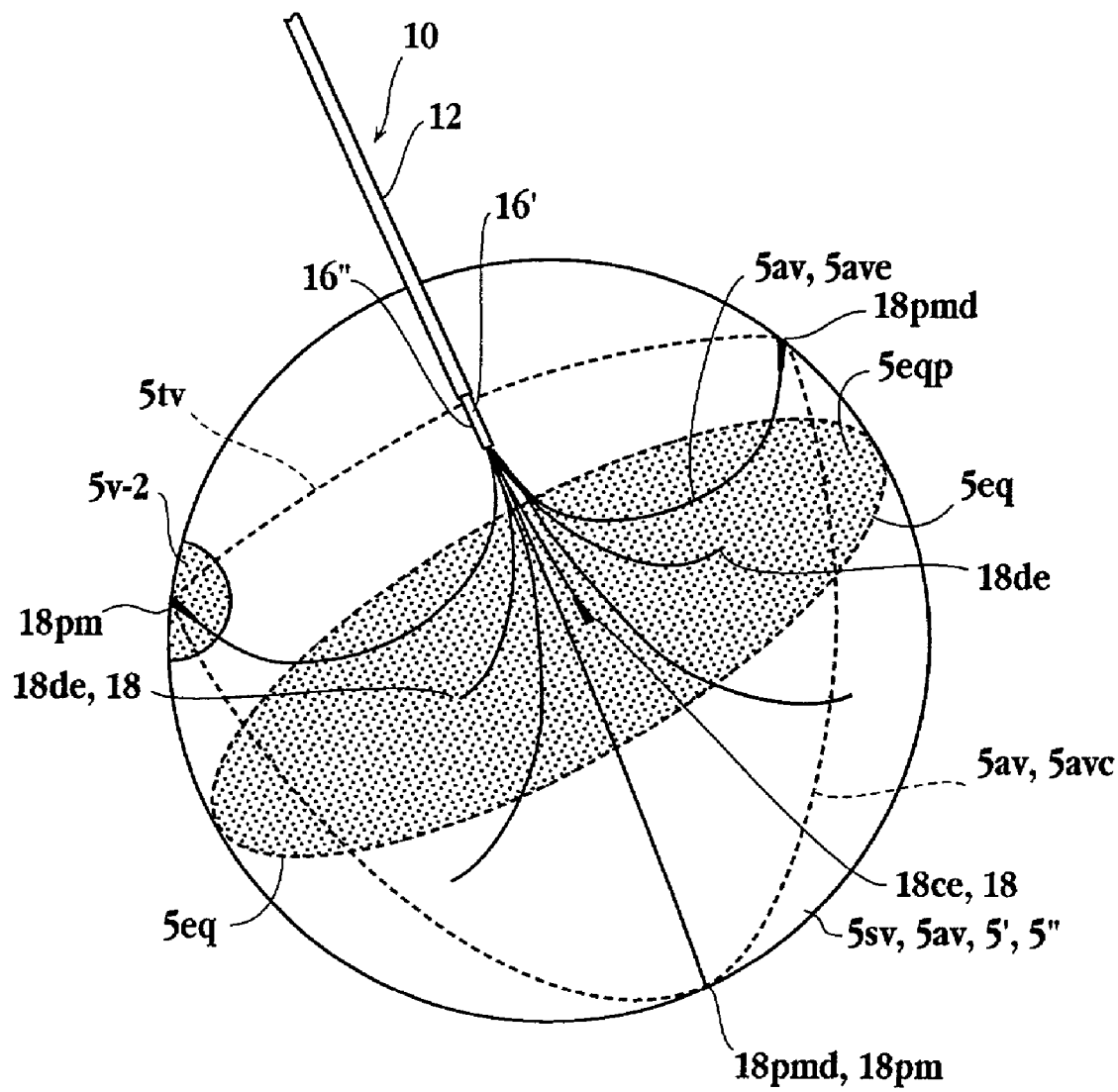
FIG. 26 is a perspective view illustrating the relative positioning of the active electrodes to define a tetrahedron shaped sampling volumes bounded by a spherical ablation volume.

Referring to FIG. 26, in an embodiment the passive arrays are positioned to define a tetrahedron or pyramid 5*tv* which is approximately circumscribed by a sphere which can approximately correspond to the ablation volume 5*av*. In this and other embodiments the ends 18*de* of the active array or electrodes 18 can be positioned approximately on the plane of 5*eqp* of the equator 5*eq* of the selected ablation volume. Preferably, the distal ends 18*pmd* of passive members 18*pm* are positioned above and below this plane. In related embodiments the central electrode 18*ce* can be positioned above plane 5*eqp* while in other embodiments one or more electrodes 18 can be positioned above or below plane 5*eqp*. Further in other related embodiments, the ends 18*pmd* of the passive members 18*pm* can configured to define another geometric shape also circumscribed by a sphere including but not limited to a cube, rectangle, or oval.

Referring to FIG. 23 in preferred embodiments the deployed length 38*p* of passive elements 18*pm* are longer than the active elements or electrodes 18 such that they can be positioned more distally than the electrodes and define a larger volume than the electrodes and that larger volume substantially contains the ablation volume 5*av*. In various embodiments, the length 38*p* of the passive elements can be 0.1 to 5 cm longer than the deployed length 38 of the electrodes, preferably 0.5 to 2 cm longer and still more preferably 1 cm longer. In a specific embodiment the electrode or active array elements are approximately 2.5 cm in length and the passive array elements are approximately 3.5 cm in length. Use of passive arrays 18*pma*, with one or more passive elements 18*pm* longer than electrodes 18 provides the novel benefit of being able to monitor in real time the development and progression of the ablation volume allowing for more complete, faster and controlled ablations and in turn, a more successful clinical outcome for the patient.

Figure 27:
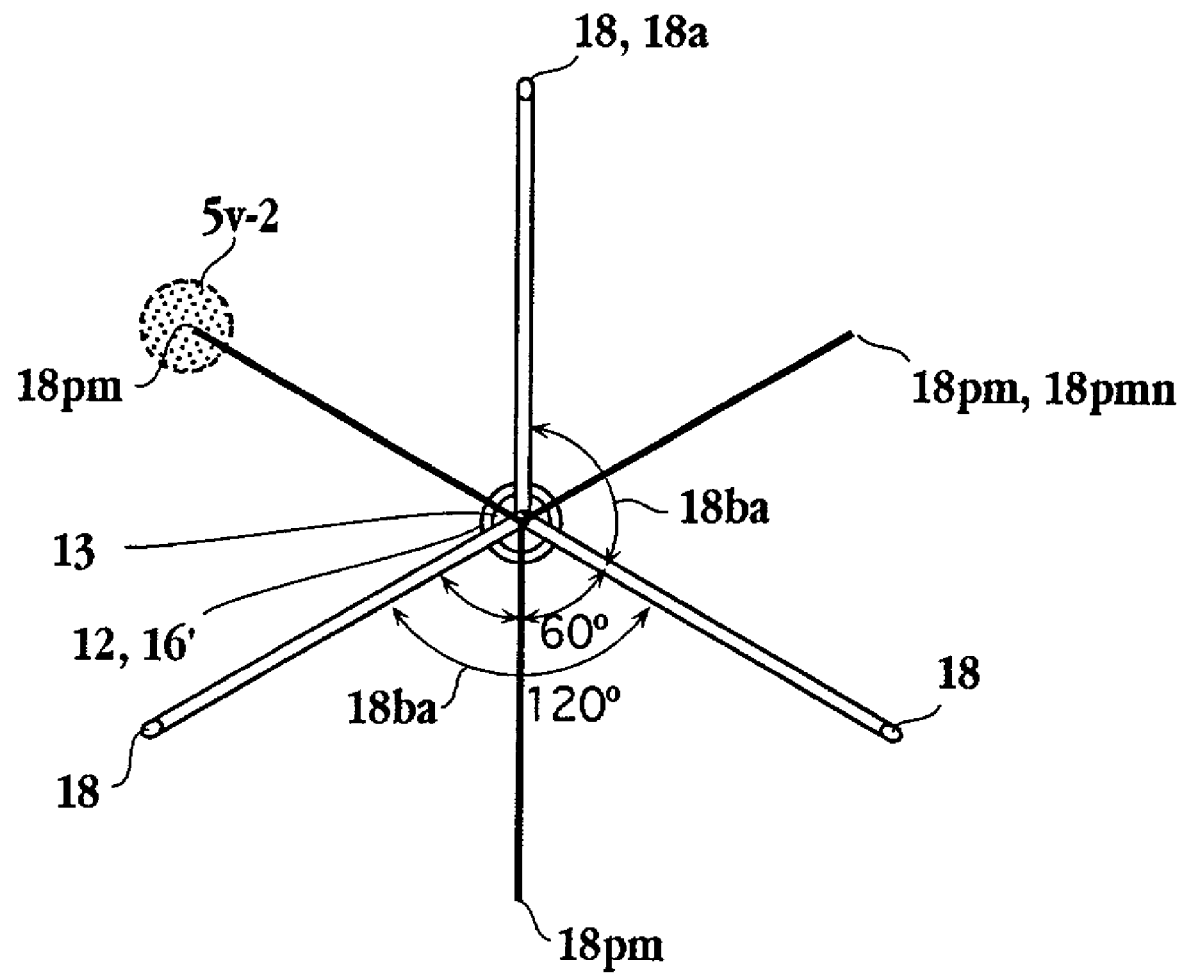
FIG. 27 is a perspective view illustrating an embodiment of the apparatus having passive and active arrays configured such that the passive elements are equally spaced between the active elements/electrodes.

Referring now to FIGS. 23 and 26, in these and related embodiments the passive elements 18*pm* can be positioned in the spaces between the electrodes or active elements so as to sample tissue volumes or zones 5*vz* at the farthest point or otherwise equidistant from any two electrodes or active elements. Referring now to FIG. 27, in an embodiment this can be optimally achieved by configuring passive arrays 18*pma* and active arrays 18*a* with an equal number of equally spaced elements and positioning the passive elements 18*pm* approximately at a point which bisects the angle 18*ba* formed between any two active elements in a plane approximately perpendicular to the longitudinal axis 12*al* of introducer 12. For example, for an embodiment having three electrodes and three passive elements the passive elements would be positioned at an angle 18*ba* of approximately 60° with respect to each of the three electrodes. Similarly for an embodiment having four passive elements and four electrodes angle 18*ba* would be approximately 45°.

Use of passive arrays positioned in zones 5*vz* provides the benefit of a higher confidence of a complete and uniform ablation in that zones 5*vz* are typically the last to reach a temperature necessary to cause ablation and/or cell necrosis and as such are the most difficult or challenging areas to ablate using RF energy. Further, the use of passive elements 18*pm* eliminates any signal artifacts and/or hysteresis that might occur as result of positioning sensors 22 on the electrodes 18 or other active elements 18. Accordingly, by using passive arrays to sample ablation volume 5*av*, embodiments of the invention provide the benefit of a more representative and/or accurate sampling of tissue temperature (or other tissue property indicative of ablation) of the entire desired ablation volume and in turn a higher confidence (including a higher statistical confidence) of achieving a complete ablation. More specifically, such embodiments provide a higher statistical correlation of measured temperature to actual tissue temperature throughout a desired tissue volume and thus a higher confidence of achieving a desired treatment endpoint (as indicated by temperature or other measured tissue property).

In an embodiment of a method of the invention, passive arrays can be used to measure a temperature at the outermost portions of the ablation volume or other zones 5*vz* such that a clinical endpoint is established and energy is stopped or decreased once a selectable temperature is reached at or near those zones. Such embodiments provide the benefits of faster ablation times as well a decreased risk of damage to healthy surrounding tissue and structures including critical anatomical structures such as organs, nerves, blood vessels etc. In various embodiments the endpoint temperature can be in the range of 38 to 75° C., preferably 40 to 70° C. and still more preferably 50 to 70° C., with specific embodiments of 40, 41, 45, 50, 55, 60 and 65° C. In a related embodiment, temperature can continued to be monitored for a period of time after energy delivery is stopped and endpoint assessed by the time decay in tissue temperatures with a relatively constant post ablation tissue temperature or slower decay being indicative of endpoint.

In an embodiment the apparatus can include three or more power arrays or electrodes and three or more passive arrays. However other embodiment can comprise any number or combination of active electrodes and passive elements including, but not limited to (i) two or more electrodes and two or more passive elements; (ii) three or more electrodes and two or more passive elements; (iii) two or more electrodes and three or more passive elements; (iv) two or more electrodes and one or more passive elements; (v) one or more electrode and two or more passive elements; (vi) more electrodes than passive elements; (vii) more passive elements than electrodes; and (viii) and an equal number of passive elements and active elements. Further in various embodiments the exact number of the electrodes and passive elements as well as their defined volume (e.g. spherical, oval,) can be selectable by the physician depending upon factors such as the size and shape of the tumor, consistency and type of tumor (e.g. fibrous, degree of vascularity, necrotic etc.), location of the tumor (e.g. liver vs. bone) and proximity of adjacent anatomical structures (e.g. blood vessels, organs etc.). This can be achieved though the use of a multiplexing device described herein, coupled to one or more electrodes and passive elements (so as to be able to switch them on or off) or advancing or withdrawing additional electrodes and passive elements through elongated member 12 and/or through electrodes or passive elements in place at the tissue site. Also the respective ablation or sample volume defined by the plurality of electrodes and passive elements can be adjusted by the physician by advancing or retracting one or more electrodes or passive elements or rotating one or more electrodes or passive elements or a combination of both techniques.

Figure 28A:
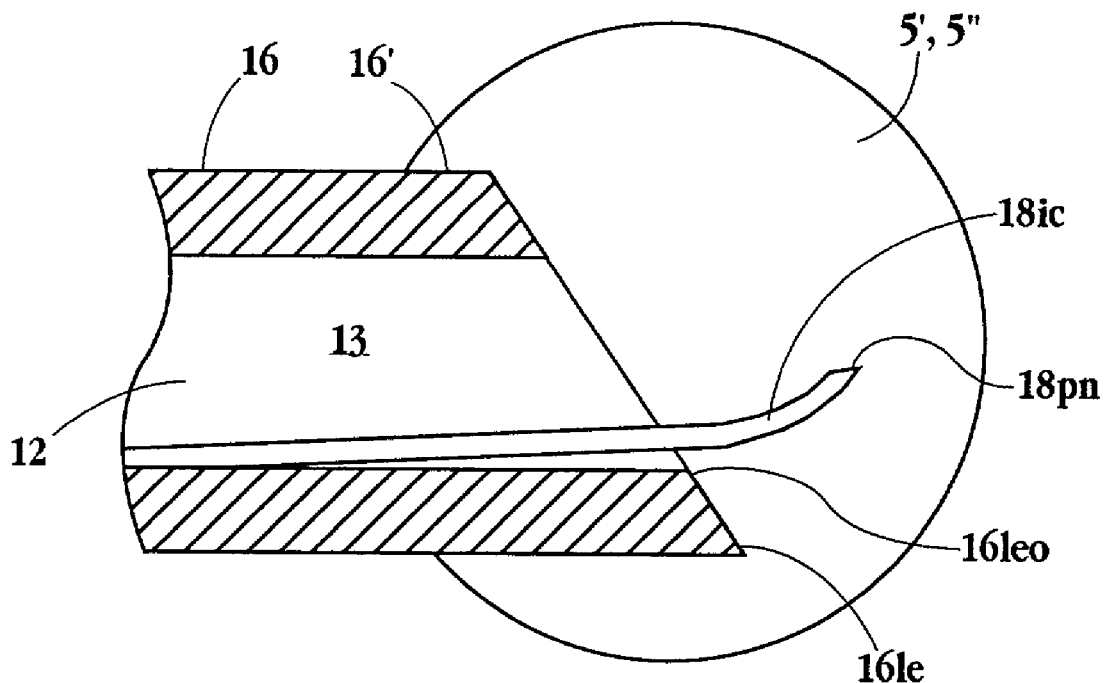
FIGS. 28a–28c are perspective views illustrating different embodiment of the trocar.
Figure 28B:
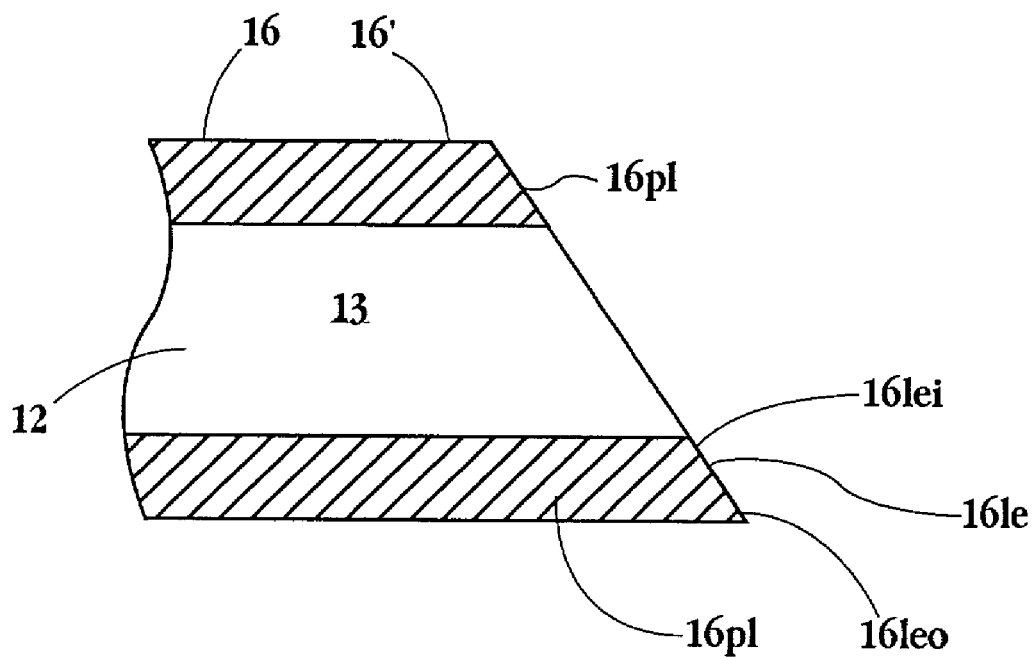
Figure 28C:
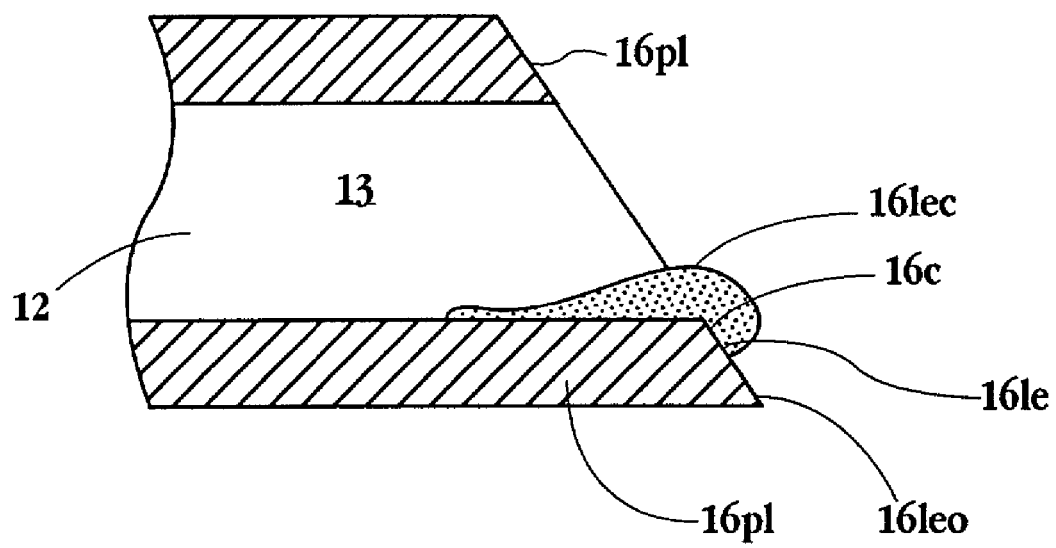

For ease of discussion introducer 12 will now be referred to as trocar 12; however all other embodiments discussed herein are equally applicable. Turning now to a discussion of trocar 12 and it use with passive arrays 18pmp, one of the potential problems in using a sharpened trocar 12 with insulative passive arrays is the scraping or braiding of the insulation 18ic on passive elements 18pm. Referring now to FIGS. 28a–28c, various embodiments of the invention provide solutions to this problem. As shown in FIG. 28a a standard trocar 12 has a tissue penetrating distal end 16 with a sharpened leading edge 16le. This sharpened leading edge can cause scraping or scything of the insulation layer of one or more passive member 18pm as the passive member pass over it during deployment to the tissue site 5".

In various embodiments all or a portion of leading edge 16le can be smoothed so as reduce or eliminate its propensity to abrade or cut insulation layer 18ic. In an embodiment shown in FIG. 28b, the leading edge 16le is only smoothed over all or a portion of its inner surface 16lei still leaving a sharpened outer surface 16leo. This embodiment provides the benefit of allowing passive member 18pm to pass over and through leading edge 16le without being abraded or cut and still permits trocar tip 16 to be tissue penetrating (e.g. the cutting edge 16leo is substantially preserved). In one embodiment inner leading 16lei is radiused using machining casting, molding or EDM methods known in the art. In another embodiments it can be polished smooth using metal polishing methods known in the art or EDM methods known in the art. The edge 16le can also be deburred using deburring methods known in the art.

In various embodiment inner leading edge 16lei can have a radius of curvature in the range of 0.0001 to 0.2 inches with specific embodiments of 0.0005, 0.001, 0.005, 0.0.01, 0.05 and 0.1 inches. In another embodiment shown in FIG. 28c, inner leading edge 16lei can be smoothed or otherwise made non scything by virtue of an applied coating 16c which can be a lubricous polymer coating known in the art such as TEFLON and the like or a hard smooth coating such as polycarbonate, acrylic and the like. Coating 16c can applied to all or a portion of leading edge 16le as well as distal tip area 16 but is preferably only substantially applied to inner leading edge 16lei. In still another alternative embodiment, the problem of insulating scything can be solved using a hardened or high strength insulative coating known in the art such as polycarbonate, LUCITE, acrylic or high strength polyimide. In a related embodiment, all or a portion of trocar distal end 16 can be fabricated from molded or machined plastic or elastomer that is configured to have sufficient rigidity, column strength and related material properties to penetrate and be advanced into tissue, but is also configured to have a radiused or smooth inner leading edge 16lei that is substantially non-scything. Plastic distal end 16pl can be attached to the body of introducer 12 using adhesive bonding, ultrasonic welding, butt joining, crimping or other tube joining method known in the medical device arts. Suitable materials for plastic distal end 16pl include polycarbonate, high-density polyethylene, acrylic and other rigid medical plastics known in the arts.

Figure 29:
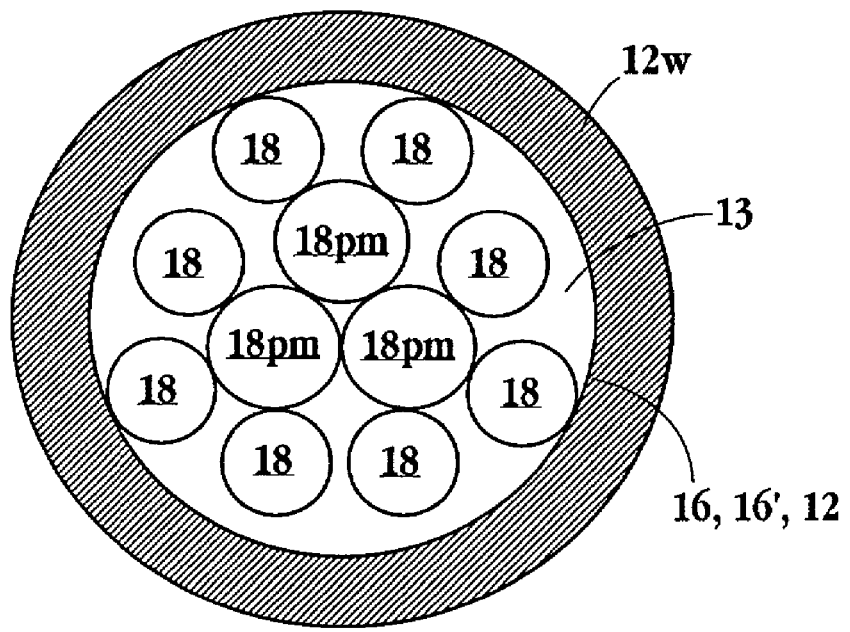
FIG. 29 is a frontal view illustrating an embodiment of the apparatus with a packing arrangement of active and passive member configured to prevent the passive members from contacting and being scythed or abraded by the sharpened edges of the trocar.

In other embodiments, insulative scything can be reduced or prevented via the geometric arrangement of the passive member and electrodes as they exit the trocar tip 16. Referring now to FIG. 29, in an embodiment the passive members 18pm and electrodes 18 can be packed or otherwise arranged such that the passive members 18pm do not pass over leading edge 16le as they exit trocar tip 16. In this and related embodiments the passive members 18pm and electrodes 18 can be packed or bundled in a substantially circular arrangement 50 approximating the arrangement of a multiwire cable with passive members 18pm placed within the interior 50i of the arrangement surrounded by active members or electrodes 18 such that the passive members do not pass do not contact in the interior surface 16is of distal end 16 including leading edge 16le. In various embodiments the packing of electrodes around passive members 18mpm can be substantially hexagonal in order to maximize packing density, in another embodiment the packing arrangement can be octagonal. In one embodiment three passive members 18pm are surrounded by eight or more electrodes 18. The maintenance of passive members 18pm within the interior 50i of packing 50 can facilitated by joining passive members 18pm and electrodes 18 at proximal locations that remain within introducer 12 using soldering, adhesive bonding or other wire bundling method known in the art.

Figure 30:
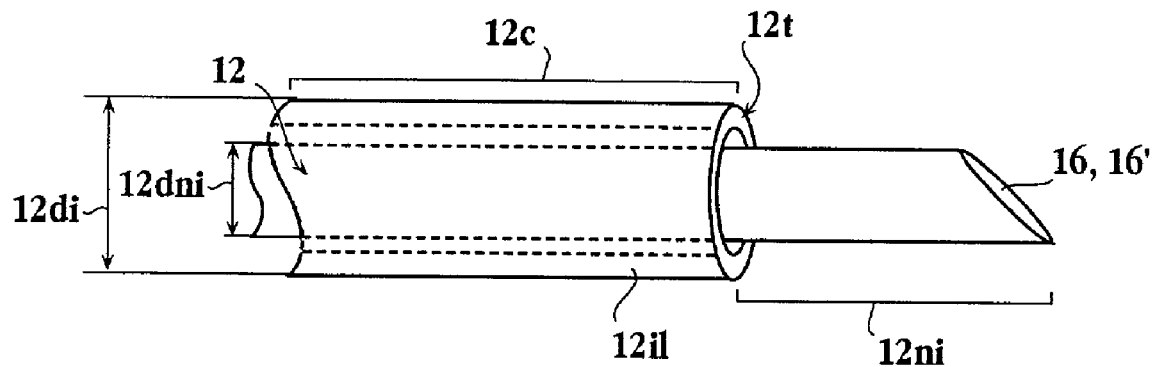
FIG. 30 is lateral view illustrating an embodiment of the trocar having an abrupt transition from the insulate to non-insulated trocar sections
Figure 31:
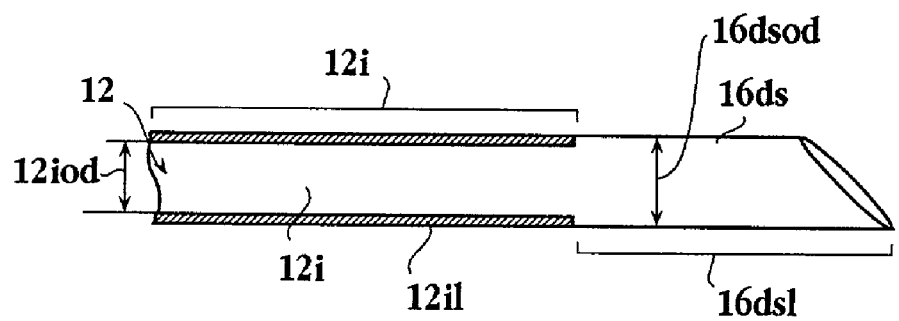
FIG. 31 is lateral view illustrating an embodiment of the trocar having a stepped distal end with a diameter configured to achieve a smooth transition form the insulated to non insulates trocar section.

Referring now to FIGS. 30 and 31, in various embodiments trocar 12 has electrically insulated and non-insulated sections 12i and 12ni. Non-insulated section 12ni is conductive and tissue ablation can occur proximate to this section. However as shown in FIG. 30, the transition 12t from section 12i to 12ni can be abrupt due to the stepdown decrease in trocar outer diameter (going from 12di to 12dni) resulting from the end of the insulation layer 12il. Such an abrupt transition 12t can increase axial resistance or force necessary to insert and position trocar 12 into tissue position distal end 16 at the target tissue site. In an embodiment shown in FIG. 31, the transition 12t can be eliminated or substantially reduced by configuring a distal section 16ds of trocar 12 to have a larger diameter 16d than the remainder of trocar 12 such that distal section 16ds is substantially flush with the insulative layer 12il on the body of trocar 12 (e.g., distal end diameter 16d is substantially equivalent to diameter 12di of section 12i).

Distal section 16ds can be made of the same material as trocar 12 (e.g., stainless steel, 304 steel and the like) and fabricated using metal, machining, molding or forging methods known in the art. Section 16ds can be integral with trocar section 12i or alternatively can be joined to section 12i using soldering, brazing, crimping or other metal joining methods known in the art. Configuring distal section 16ds flush with trocar section 12i reduces the force necessary to insert the trocar into tissue and also smoothes out the insertion process giving the physician a better tactile feel for properly positioning the trocar at the target tissue site. Further these and related embodiments of a stepped trocar distal end provide the benefit of facilitating insertion and positioning of trocar 12 and distal section 16ds to the target tissue site, increasing the placement accuracy of distal section 16ds, reducing procedure time and increasing procedure efficacy. In an embodiment, distal section 16ds can have an outer diameter 16dsod of 0.087 to 0.089 inches while the outer diameter 12iod of the non-insulated trocar is 0.080 to 0.082 inches, and insulation layer 12il thickness of between 0.0025 to 0.0045 inches. The length 16dsl of distal section 16ds can be in the range of 6.5 to 8.5 mm.

Figure 32:
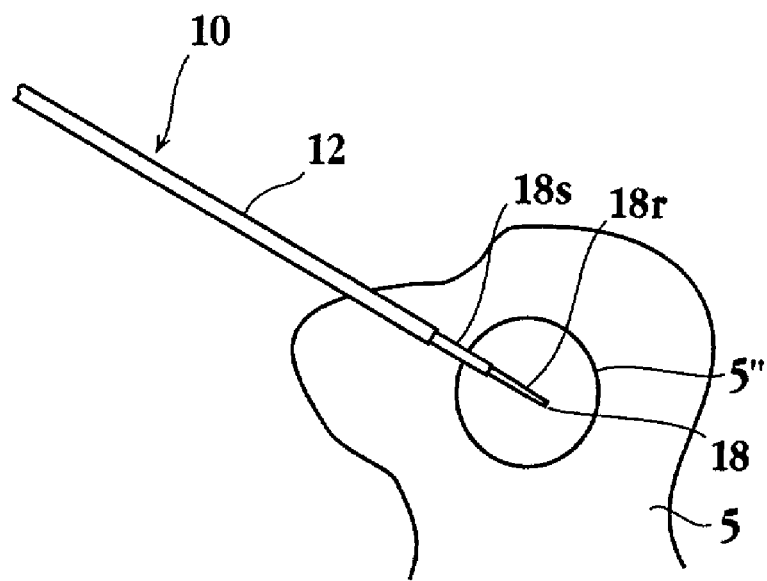
FIG. 32 is a lateral view illustrating an embodiment of an energy delivery device with a radioactive section and its use in an embodiment of a method of the invention.

Referring now to FIG. 32, in an embodiment, all or a portion of one or more of the energy delivery devices 18 can include a radioactive portion 18r. Radioactive portion 18r is fabricated from a radioactive material having sufficient radioactive strength (e.g., curies) to necrose, ablate, ionize or otherwise kill tumorous tissue 5" at issue site 5'. In related embodiments, a radioactive absorbing sheath 18s can be configured to be slidably positioned over radioactive portion 18r so as to control the exposed length 18r' of radioactive portion 18r and thus the dose of radioactivity delivered to the tumor mass 5".

The radioactive material in section 18r can include gamma, alfa-or beta-emitting materials. Suitable gamma emitters include, but are not limited to. Cobalt-60, Iodine-131, Iodine-123, Indium-111, Gallium-67 and Technetium-99 m. Suitable beta emitting particles include tritium. The amount of radioactive material in portion 18r can be configured to deliver 0.01 to 100 rads of radiation with specific embodiments of 0.1, 0.25, 0.5, 1, 10 and 50 rads. The amount of radiation delivered can measure using a radiation sensor 22 coupled to energy delivery device 18 or introducer 12. Radioactive absorbing sheath 18s can include one or more radioactive absorbing materials known in the art that are impregnated or otherwise integral to a flexible metal or polymer layer. Such radioactive absorbing materials include but are not limited to lead, iron or graphite. In an embodiment, the radioactive absorbing material can be fabricated into a braided wire or sheath incorporated into the wall of sheath 18s using catheter production methods known in the art.

In use, radioactive section 18r provides the patient with the benefit of radiation therapy having a highly targeted delivery of radioactivity to the tumor mass while minimizing injury to surrounding tissue. The radiation can be delivered alone or as an adjunct to another ablative treatment describe herein (before during or after such treatment) to sensitize cancer cells to other forms of necrotic therapy or otherwise increase the probability of killing cancerous tissue. The dose of radiation can at such level for example below 1 rad that it has no affect on healthy or untreated tissue but when combined with another energetic therapy serves to surpass a lethal threshold for the selected tumorous tissue. Such therapy provides the benefit of an increased probability of killing all the cancer cells at the tumor site and thus an improved clinical outcome for the patient.

Figure 33:
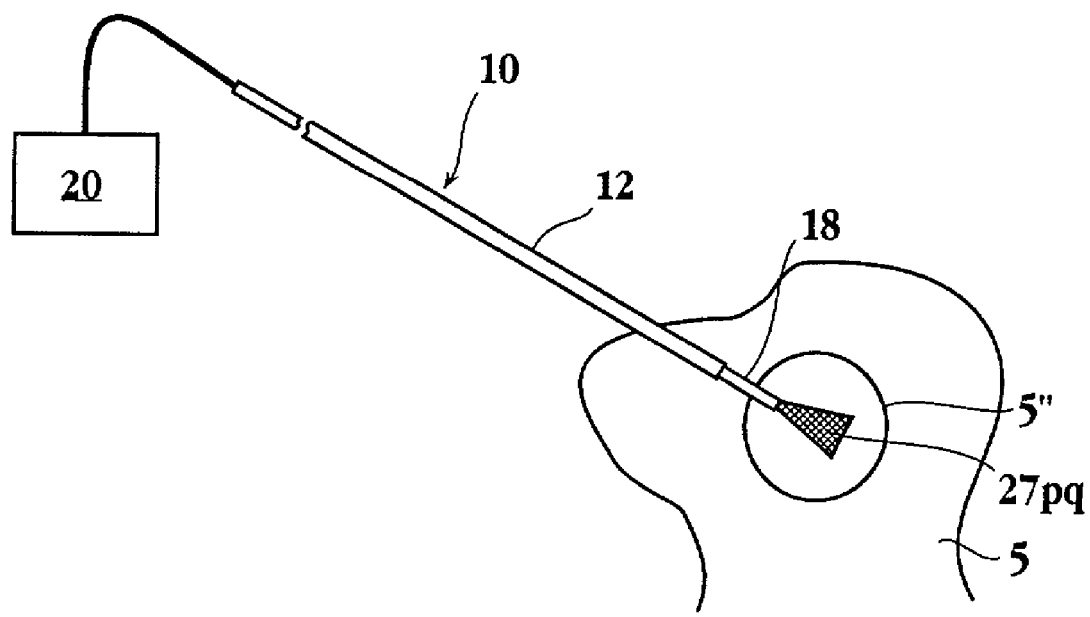
FIG. 33 is a lateral view illustrating use of photo-therapeutic agents in an embodiment of a method of the invention.

Other embodiments of the invention can employ photo-dynamic therapy described herein to treat tumors. Referring to FIG. 33 (a perspective view illustrating an embodiment employing photo activated agents), in such embodiments apparatus 10 can be configured to deliver a phototherapeutic agent 27pa also known as a photodynamic agent 27pa to the target tissue site. Agent 27a can be configured to selectively be taken up and/or otherwise selectively bind to tumor mass 5". Once the agent is delivered and taken up by the tumor 5" an optical embodiment of the energy delivery device is used to delivery optical radiation to activate therapeutic agent 5" and cause the necrosis or ablation of tumor mass 5". However, prior to photo-activation agent 27pa remains in an inert or nontoxic state. Examples of optical energy delivery devices 18 include optical fibers, light pipes, wave-guides and the like. Examples of photo-therapeutic agents include chlorophyll-based compounds such as Bacteriochlorophyll-Serine and texaphyrin based compounds such as lutetium texaphyrin manufactured by Pharmacyclics, Inc. (Sunnyvale, Calif.). Examples of activating radiation include radiation in the infrared, near infrared and ultraviolet range of the spectrum. Such radiation can be delivered by the optical energy delivery devices described herein as well as other optical delivery devices known in the art. In an embodiment, agent 27pa can be delivered as a fluid through a bone access device or bone biopsy needle directly to the tumor site 5" or through the Haversian canals.

In various embodiments, photo-dynamic therapy can be conducted prior, concurrently or after with thermal ablative therapy such as RF ablative therapy. In a related embodiment, photo-agent 27pa can also be configured to increase the hyperthermic affect of RF or other electromagnetic energy delivered to tumor mass 5" or otherwise selectively sensitize tumor tissue to the necrotic affects of hyperthermic tumor treatment such as RF ablative treatment. In a specific embodiment photo-agent 27pa is configured to be repelled by bone tissue including calcium-based tissue or collagen based tissue and thus increase the agents specificity for tumorous tissue. In another embodiment the photosentisizing agent 27pa can be configured to be activated by a wavelength of light that is reflected by bone tissue yet absorbed darker tumorous tissue. This and related embodiments provide the benefit of an agent 27pa that is highly specific to tumor tissue yet has little or no affect on healthy bone. Further, the use of agent 27pa allows the level of hypothermic treatment to be titrated to the size and type of tumor tissue. This can be accomplished by using a spectrum of agent's 27pa that increases or decreases the level of tumor sensitization as needed.

Other embodiments of the invention can combine thermal or other ablative therapy described herein with chemotherapy or other medicinal based therapy. Apparatus 10 can be used to deliver various chemotherapeutic or medicinal agents along or in combination before, during or post ablation. One such family of agent includes antisense-based compounds configured to inhibit the metabolism by the liver (by inhibition of liver enzymes) of various chemotherapeutic agents and thus extend their biological half-life (e.g. effectiveness) while minimizing side-affects. An example of such a compound includes NEUGENE® antisense compound manufacture by AVI BioPharma Inc (Portland Oreg.). Such compounds can be delivered directly to the liver using apparatus 10 or other drug delivery device described herein or known in the art.

Figure 34:
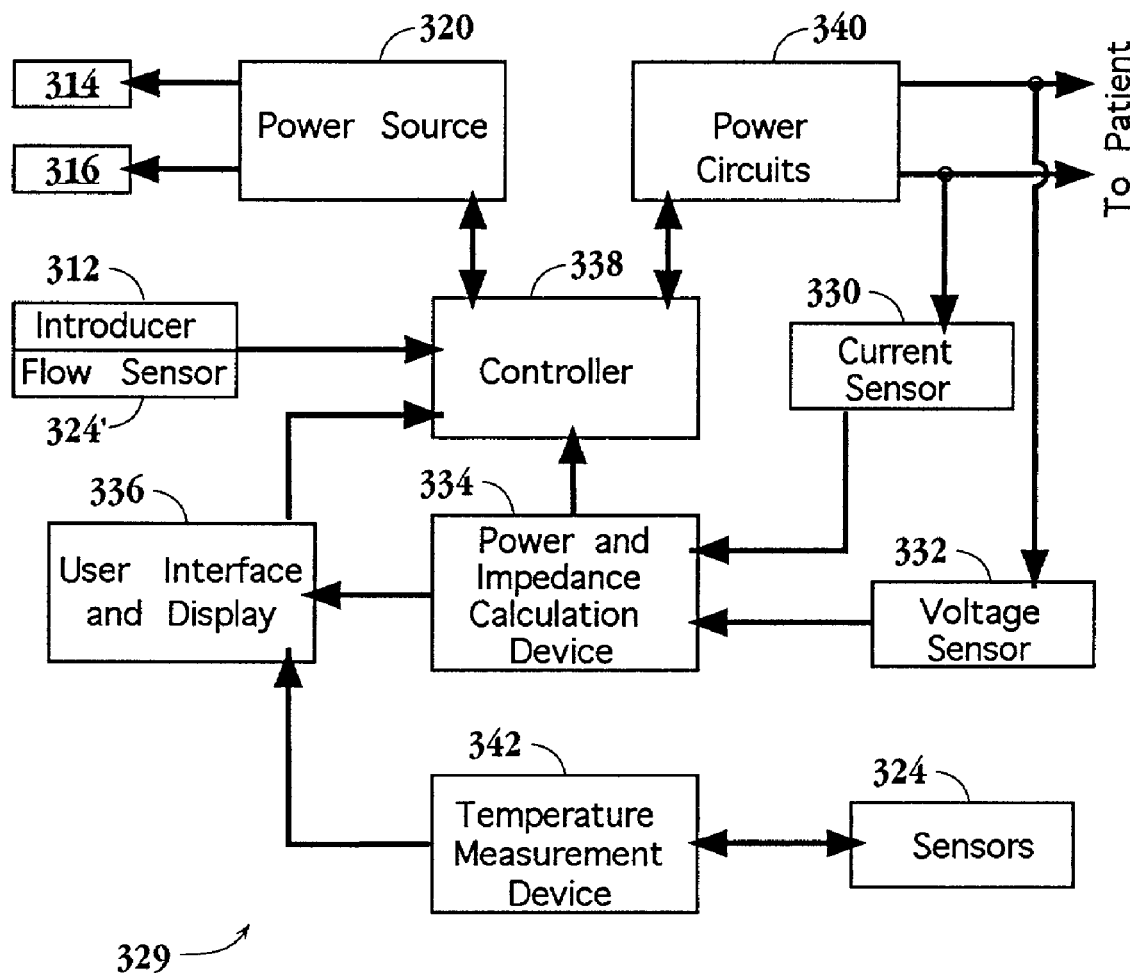
FIG. 34 is a block diagram illustrating the inclusion of a controller, energy source and other electronic components of the present invention.
Figure 35:
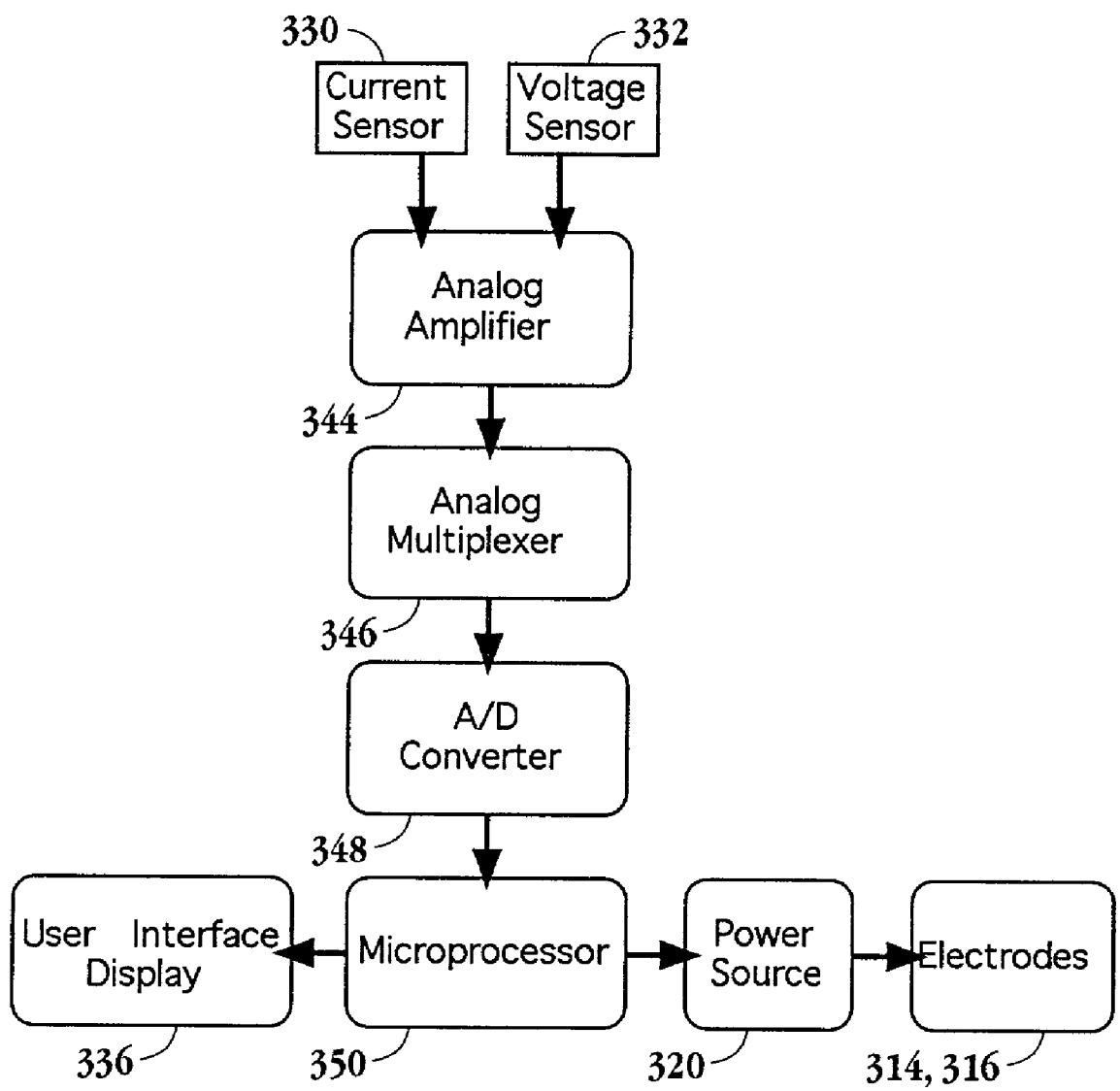
FIG. 35 is a block diagram illustrating an analog amplifier, analog multiplexer and microprocessor used with the present invention.

Referring now to FIGS. 34 and 35, a feedback control system 329 can be connected to energy source 320, sensors 324 and energy delivery devices 314 and 316. Feedback control system 329 receives temperature or impedance data from sensors 324 and the amount of electromagnetic energy received by energy delivery devices 314 and 316 is modified from an initial setting of ablation energy output, ablation time, temperature, and current density (the "Four Parameters"). Feedback control system 329 can automatically change any of the Four Parameters. Feedback control system 329 can detect impedance or temperature and change any of the Four Parameters. Feedback control system 329 can include a multiplexer to multiplex different antennas, a temperature detection circuit that provides a control signal representative of temperature or impedance detected at one or more sensors 324. A microprocessor can be connected to the temperature control circuit.

The following discussion pertains particularly to the use of an RF energy source and lung treatment/ablation apparatus 10. For purposes of this discussion, energy delivery devices 314 and 316 will now be referred to as RF electrodes/antennas 314 and 316 and energy source 320 will now be an RF energy source. However it will be appreciated that all other energy delivery devices and sources discussed herein are equally applicable and devices similar to those associated with lung treatment/ablation apparatus 10 can be utilized with laser optical fibers, microwave devices and the like. The temperature of the tissue, or of RF electrodes 314 and 316 is monitored, and the output power of energy source 320 adjusted accordingly. The physician can, if desired, override the closed or open loop system.

The user of apparatus 10 can input an impedance value that corresponds to a setting position located at apparatus 10. Based on this value, along with measured impedance values, feedback control system 329 determines an optimal power and time needed in the delivery of RF energy. Temperature is also sensed for monitoring and feedback purposes. Temperature can be maintained to a certain level by having feedback control system 329 adjust the power output automatically to maintain that level.

In another embodiment, feedback control system 329 determines an optimal power and time for a baseline setting. Ablation volumes or lesions are formed at the baseline first. Larger lesions can be obtained by extending the time of ablation after a center core is formed at the baseline. The completion of lesion creation can be checked by advancing energy delivery device 316 from distal end 16' of introducer 12 to a position corresponding to a desired lesion size and monitoring the temperature at the periphery of the lesion such that a temperature sufficient to produce a lesion is attained.

The closed loop system 329 can also utilize a controller 338 to monitor the temperature, adjust the RF power, analyze the result, and then modulate the power. More specifically, controller 338 governs the power levels, cycles, and duration that the RF energy is distributed to electrodes 314 and 316 to achieve and maintain power levels appropriate to achieve the desired treatment objectives and clinical endpoints. Controller 338 can also in tandem govern the delivery of electrolytic, cooling fluid and, the removal of aspirated tissue. Controller 338 can also in tandem monitor for pressure leaks (via pressure flow sensors 324') through introducer 312 tending to cause pneumothorax and actuate coupled control valves to block the fluid path causing the leak and/or initiate the delivery of sealant and/or energy at the target tissue site to seal the leak. Controller 338 can be integral to or otherwise coupled to power source 320. The controller 338 can be also be coupled to an input/output (I/O) device such as a keyboard, touchpad, PDA, microphone (coupled to speech recognition software resident in controller 338 or other computer) and the like.

Referring now to FIG. 34, all or portions of feedback control system 329 are illustrated. Current delivered through RF electrodes 314 and 316 (also called primary and secondary RF electrodes/antennas 314 and 316) is measured by a current sensor 330. Voltage is measured by voltage sensor 332. Impedance and power are then calculated at power and impedance calculation device 334. These values can then be displayed at a user interface and display 336. Signals representative of power and impedance values are received by controller 338 which can be a microprocessor 339.

A control signal is generated by controller 338 that is proportional to the difference between an actual measured value, and a desired value. The control signal is used by power circuits 340 to adjust the power output in an appropriate amount in order to maintain the desired power delivered at the respective primary and/or secondary antennas 314 and 316. In a similar manner, temperatures detected at sensors 324 provide feedback for maintaining a selected power. The actual temperatures are measured at temperature measurement device 342, and the temperatures are displayed at user interface and display 336. A control signal is generated by controller 338 that is proportional to the difference between an actual measured temperature, and a desired temperature. The control signal is used by power circuits 340 to adjust the power output in an appropriate amount in order to maintain the desired temperature delivered at the respective sensor 324. A multiplexer 346 can be included to measure current, voltage and temperature, at the numerous sensors 324 as well as deliver and distribute energy between primary electrodes 314 and secondary electrodes 316.

Controller 338 can be a digital or analog controller, or a computer with embedded, resident or otherwise coupled software. In an embodiment controller 338 can be a Pentium® family microprocessor manufacture by the Intel® Corporation (Santa Clara, Calif.). When controller 338 is a computer it can include a CPU coupled through a system bus. On this system can be a keyboard, a disk drive, or other non-volatile memory systems, a display, and other peripherals, as are known in the art. Also coupled to the bus are a program memory and a data memory. In various embodiments controller 338 can be coupled to imaging systems, including but not limited to ultrasound, CT scanners (including fast CT scanners such as those manufacture by the Imatron Corporation (South San Francisco, Calif.), X-ray, MRI, mammographic X-ray and the like. Further, direct visualization and tactile imaging can be utilized.

User interface and display 336 can include operator controls and a display. In an embodiment user interface 336 can be a PDA device known in the art such as a Palm® family computer manufactured by Palm® Computing (Santa Clara, Calif.). Interface 336 can be configured to allow the user to input control and processing variables, to enable the controller to generate appropriate command signals. Interface 336 can also receives real time processing feedback information from one or more sensors 324 for processing by controller 338, to govern the delivery and distribution of energy, fluid etc.

The output of current sensor 330 and voltage sensor 332 is used by controller 338 to maintain a selected power level at primary and secondary antennas 314 and 316. The amount of RF energy delivered controls the amount of power. A profile of power delivered can be incorporated in controller 338, and a preset amount of energy to be delivered can also be profiled.

Circuitry, software and feedback to controller 338 results in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 324. A controller 338 can be incorporated into feedback control system 329 to switch power on and off, as well as modulate the power. Also, with the use of sensor 324 and feedback control system 329, tissue adjacent to RF electrodes 314 and 316 can be maintained at a desired temperature for a selected period of time without causing a shut down of the power circuit to electrode 314 due to the development of excessive electrical impedance at electrode 314 or adjacent tissue.

Referring now to FIG. 35, current sensor 330 and voltage sensor 332 are connected to the input of an analog amplifier 344. Analog amplifier 344 can be a conventional differential amplifier circuit for use with sensors 324. The output of analog amplifier 344 is sequentially connected by an analog multiplexer 346 to the input of A/D converter 348. The output of analog amplifier 344 is a voltage that represents the respective sensed temperatures. Digitized amplifier output voltages are supplied by A/D converter 348 to a microprocessor 350. Microprocessor 350 may be Model No. 68HCII available from Motorola. However, it will be appreciated that any suitable microprocessor or general purpose digital or analog computer can be used to calculate impedance or temperature.

Microprocessor 350 sequentially receives and stores digital representations of impedance and temperature. Each digital value received by microprocessor 350 corresponds to different temperatures and impedances. Calculated power and impedance values can be indicated on user interface and display 336. Alternatively, or in addition to the numerical indication of power or impedance, calculated impedance and power values can be compared by microprocessor 350 with power and impedance limits. When the values exceed predetermined power or impedance values, a warning can be given on user interface and display 336, and additionally, the delivery of RF energy can be reduced, modified or interrupted. A control signal from microprocessor 350 can modify the power level supplied by energy source 320 to RF electrodes 314 and 316. In a similar manner, temperatures detected at sensors 324 provide feedback for determining the extent and rate of (i) tissue hyperthermia (ii) cell necrosis; and (iii) when a boundary of desired cell necrosis has reached the physical location of sensors 324.

Platonic Solid Embodiments: An embodiment of a method of the invention provides a method to utilize platonic solid geometry to minimize the number of individual ablations required to produce a collective ablation volume larger than any single ablation volume. More specifically the embodiment provides a method to maximize the effect of overlapping ablations to treat tumors larger than the capabilities of current commercially available products. This and related embodiments are also applicable to the design of a multi-electrode device where each electrode will create a sub-lesion in order to create a meta-lesion that is the combination of the smaller lesions.

Specific embodiments provide method for using one or more of a series of optimal geometries used as a template for positioning overlapping ablations to create a meta ablation volume. In order to find the most efficient geometry for the placement of the sub-lesions it is obvious that the more symmetric the pattern the larger the meta-lesion will be for a given number of sub-lesions at a given size.

Platonic solids are composed of regular convex polygons that have the same number of polygons meeting at each corner. In all Platonic solids the number of sides is equal to or less than the number of vertices. Because the goal is to reduce the number of sub-lesions required, the sub-lesions will be placed on each face of the platonic solid and not at the vertices.

Figure 36:
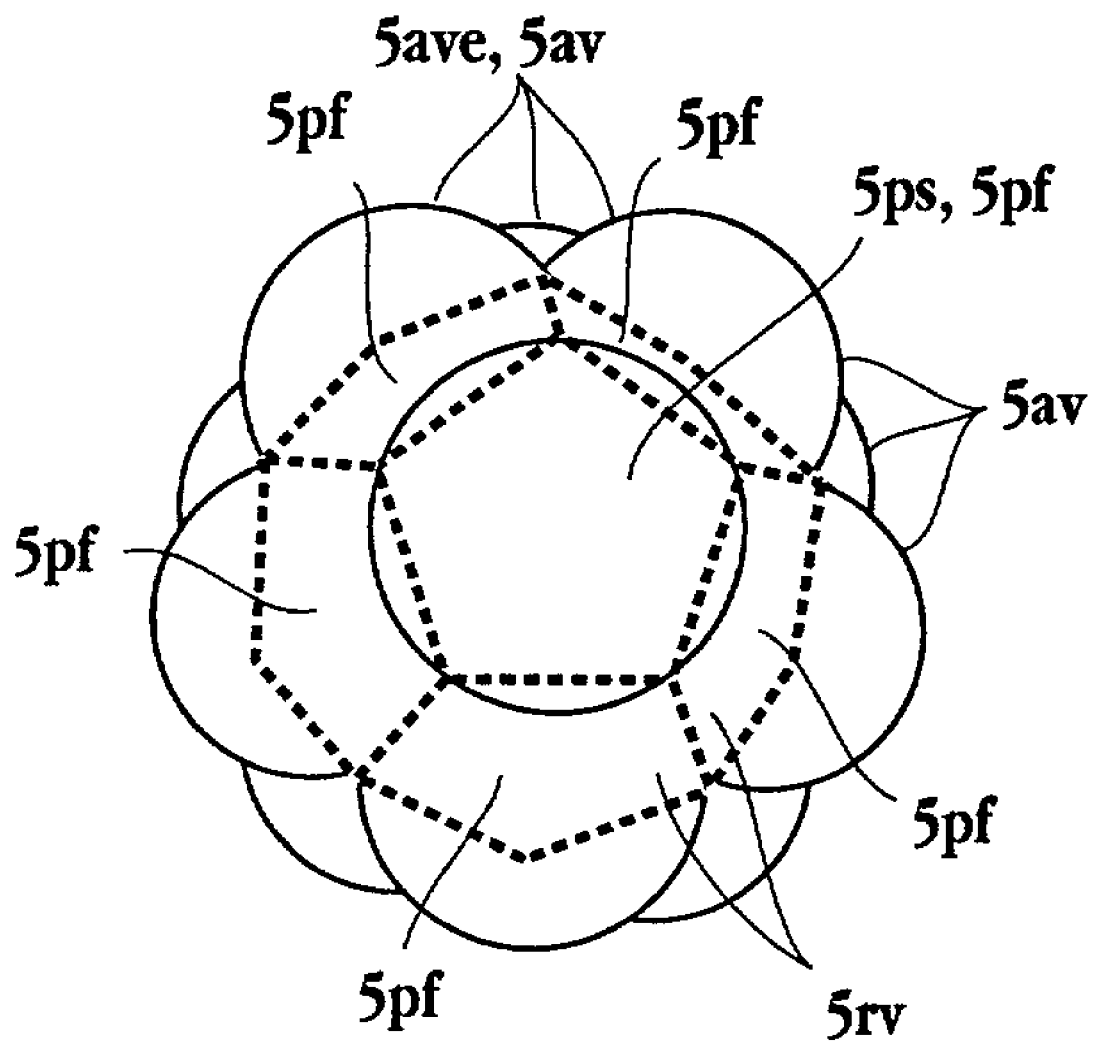
FIG. 36 is a perspective view illustrating the use of platonic solids to optimize ablation volume in a method of the invention.
Figure 37A:
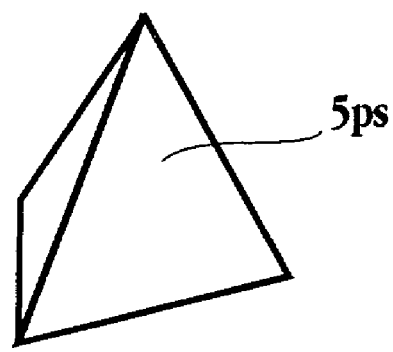
FIGS. 37a–37e are perspective views illustrating various platonic solids applicable to the embodiment of FIG. 36.
Figure 37B:
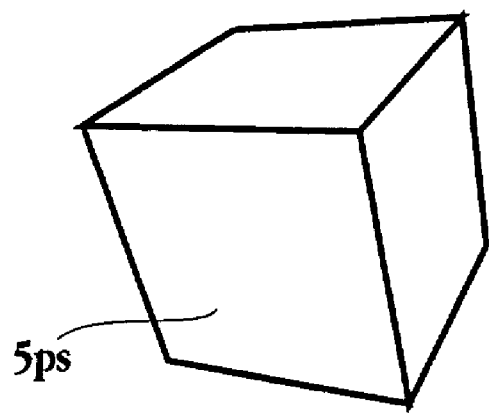
Figure 37C:
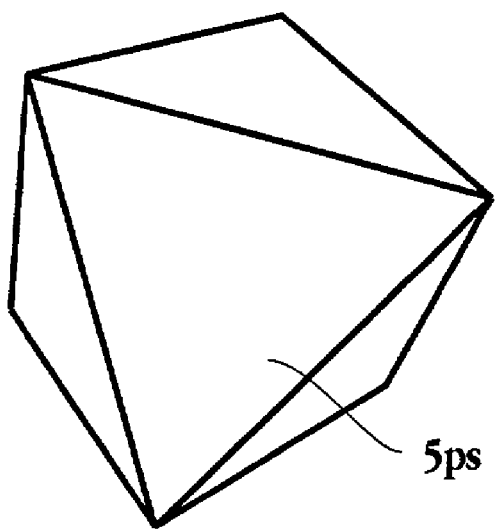
Figure 37D:
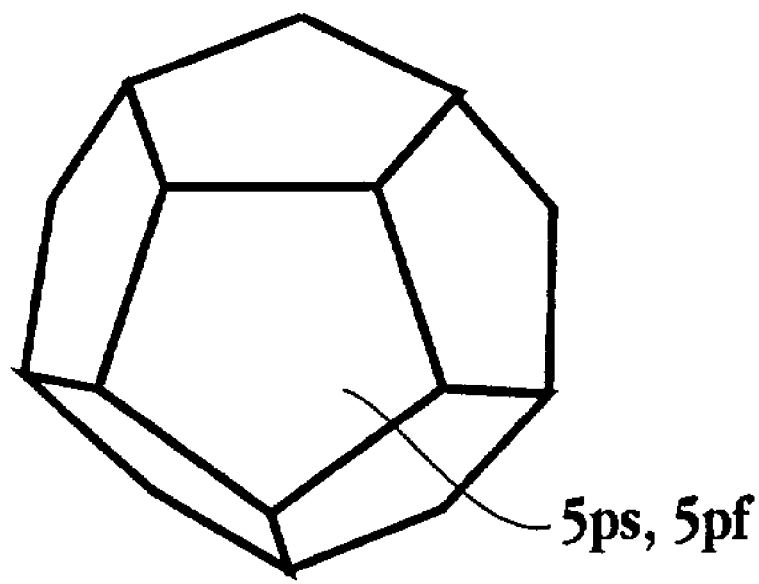
Figure 37E:
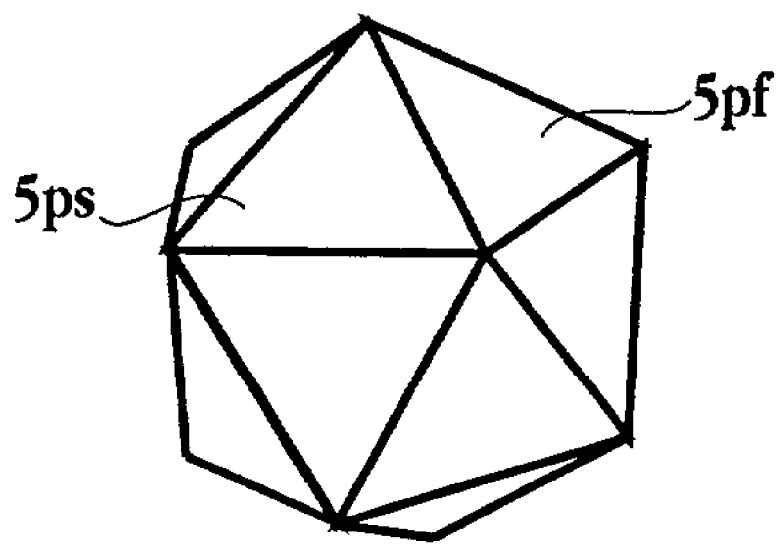

Referring now to FIG. 36 in an embodiment a platonic solid 5ps is used as a template or reference volume 5rv with which to place individual or sublesions 5ave in order to create a larger collective lesion or meta lesion 5avc. With the center of the sub-lesion 5ave on the center of the face of the platonic solid 5ps and the diameter of the sub-lesion circumscribing the vertices of the face of the platonic solid, a meta-lesion is formed that is defined by the diameter of the platonic solid, as measured between opposite corners. Referring to FIGS. 37a–37e example platonic solids 5ps which can be used as the template or reference volume 5rv include, but are not limited to, Tetrahedron, Cube, Octahedron, Dodecahedron, and Icosahedron.

For platonic solids with 8 or fewer faces the sub-lesions overlap in the center of the meta-lesion. For platonic solids with 12 or more sides an additional sub-lesion in the center of the meta-lesion is required for a complete volumetric coverage. Using this concept and geometry it is possible to construct a table outlining the minimum number of ablations required to create a meta-lesion.

| Size/Number | 4 | 6 | 8 | 12* | 20* |
| --- | --- | --- | --- | --- | --- |
| 1 | 1.06 | 1.23 | 1.23 | 1.65 | 1.9 |
| 3 | 3.18 | 3.69 | 3.69 | 4.95 | 5.7 |
| 5 | 5.3 | 6.15 | 6.15 | 8.25 | 9.5 |

*One additional ablation required in the center to cause complete volumetric coverage The apparatus and method of this invention are particularly useful for o benign and cancerous tumors using of RF energy and infused fluids. It will be readily apparent to a person skilled in the art that various embodiments and combinations of embodiments of the device and method can be used to sample or ablate/destroy body tissues, tissue locations that are accessible by percutaneous or endoscopic catheters, and is not limited to the bone in the liver, lung, bone, brain and breast. Such tissue locations and organs include, but are not limited to, the heart and cardiovascular system, upper respiratory tract and gastrointestinal system as well as the bone in the liver, lung, bone, brain and breast. Application of the apparatus and method in all of these organs and tissues are intended to be included within the scope of this invention.

Also this specification discloses various catheter-based systems and methods for treating the bone and adjoining tissue regions in the body. The systems and methods that embody features of the invention are also adaptable for use with systems and surgical techniques both in the bone and other areas of the body that are not necessarily catheter-based. Furthermore, this specification is not intended to be exhaustive or to limit the invention to the precise forms disclosed. It will be apparent that various modifications, applications, and different combinations of embodiments can be made without departing from the invention as claimed.

It is claimed:
1. A tissue-ablation apparatus comprising:
   (a) an elongate delivery device having a lumen terminating at a distal end,
   (b) a plurality of electrodes carried in said device for movement between retracted positions at which the electrodes are disposed within the device's lumen, and deployed positions at which the electrodes define a tissue volume, said electrodes being operatively connected to a power source for producing ablation within said volume in response to power supplied from the power source to said electrodes,
   (c) a plurality of passive elongate sensor elements carried in said device for movement between retracted positions at which the sensor elements are disposed within the device's lumen, and deployed positions at which the sensor elements are deployed from said distal end at a plurality of angularly spaced positions at which the deployed sensor elements are distributed within said volume, said sensor elements being unable to deliver ablative energy, and (d) at least one sensor positioned on each of the elongate sensor elements for monitoring tissue ablation in said volume, wherein the supply of power to said electrodes can be regulated to control a level and extent of tissue ablation throughout said volume according to the tissue ablation monitored by said sensors.

2. The apparatus of claim 1, wherein said electrodes and sensor elements are operatively connected for movement as a unit from their retracted to their deployed positions.

3. The apparatus of claim 1, wherein said electrodes are movable between their retracted and deployed positions independent of the movement of the sensor elements.

4. The apparatus of claim 1, wherein the sensors are thermal sensors.

5. The apparatus of claim 1, wherein said electrodes are hollow-needle electrodes, allowing liquid to be injected through said electrodes into tissue, with the electrodes deployed in tissue.

6. The apparatus of claim 5, which is designed to allow controlled fluid flow through each electrode individually.

7. The apparatus of claim 5, wherein at least one electrode has a plurality of infusion ports along its distal end regions, and is covered by a sheath that is axially movable between deployment and infusion positions at which the infusion ports are covered and exposed, respectively.

8. The apparatus of claim 5, wherein at least one electrode has a plurality of infusion ports along its distal end regions, and is covered by a sheath including a fixed gap.

9. The apparatus of claim 1, wherein said power source includes a display function for displaying to a user the extent of ablation in the tissue volume, and an adjustable power function by which the user can adjust the power applied to said electrodes.

10. The apparatus of claim 1, wherein said power source is operable to automatically adjust the power level applied to said electrodes in response to information received from said sensors relating to the extent of ablation in the regions of the sensor elements.

11. The apparatus of claim 1, wherein said electrodes are hollow-needle electrodes, allowing liquid to be injected through said electrodes into tissue, with the electrodes deployed in tissue, and said power source includes a display function for displaying to a user the extent of ablation in the tissue volume, and an adjustable fluid-control function by which the user can adjust the rate of liquid supplied to the individual electrodes.

12. The apparatus of claim 1, wherein said electrodes are hollow-needle electrodes, allowing liquid to be injected through said electrodes into tissue, with the electrodes deployed in tissue, and said power source is operable to control the rate of liquid flow through the electrodes in response to information received from said sensor elements relating to the extent of ablation in the tissue volume.

13. The apparatus of claim 1, wherein said electrodes, when deployed, are positioned near the center of the faces of a platonic solid that defines a desired combined-electrode ablation volume.

14. The apparatus of claim 13, wherein the sensor elements, when deployed, are positioned near vertices of the platonic solid.

15. The apparatus of claim 13, for ablating a substantially spherical volume that circumscribes a pyramid, which has four electrodes that are positioned near the center of the faces of the pyramid when deployed, and four sensor elements which are placed near the vertices of the pyramid when deployed.

16. The apparatus of claim 1, which further includes a body-surface electrode adapted to be applied to the surface of a patient, and the control device is operable to apply power between the plurality of electrodes and the body-surface electrode.

17. The apparatus of claim 1, wherein said apparatus is configured to operate in a bipolar mode.

18. The apparatus of claim 1, wherein all or a portion of the elongate delivery device distal end is plastic.

19. The apparatus of claim 1, wherein all or a portion of the elongate delivery device distal end is elastomer.

20. The apparatus of claim 1, wherein said elongate delivery device is configured to have a radiused or smooth inner leading edge.

21. The apparatus of claim 1, further comprising
a control device operatively connected to said electrodes and to said sensor elements for modulating power to said electrodes in response to information received from said sensors.

22. The apparatus of claim 1, wherein said electrodes are RF electrodes adapted to be operatively coupled to a RF energy source.

23. The apparatus of claim 1, wherein said electrodes are microwave electrodes adapted to be operatively coupled to a microwave energy source.

24. The apparatus of claim 1, further including an electrically insulative sleeve positioned over all of at least some of the sensor elements.

25. The apparatus of claim 1, wherein at least some of said sensor elements are not connected to the power source.

26. The apparatus of claim 1, wherein at least some of said sensor elements are formed of a non-conductive material.

27. The apparatus of claim 1, further comprising a multiplexing device coupled to at least some of the sensor elements.

28. A tissue-ablation apparatus for connection a power source comprising:
(a) an elongate delivery device having a lumen terminating at a distal end,
(b) a plurality of electrodes carried in said device for movement between retracted positions at which the electrodes are disposed within the device's lumen, and deployed positions at which the deployed electrodes define a tissue volume, said electrodes being connected to said power for producing ablation within said volume in response to power supplied from the power source to said electrodes,
(c) a plurality of passive elongate sensor elements carried in said device for movement between retracted positions at which the sensor elements are disposed within the device's lumen, and deployed positions at which the sensor elements are deployed from said distal end at a plurality of angularly spaced positions at which the deployed sensor elements are distributed within said volume, said sensor elements being unable to deliver ablative energy, and
(d) at least one sensor positioned on each of the elongate sensor elements for monitoring tissue ablation in said volume, said sensors being connected to said power source,
wherein the supply of power to said electrodes from said power source can be regulated to control a level and extent of tissue ablation throughout said volume according to the tissue ablation monitored by said sensors.

* * * * *